United States Patent
Ingalhalikar et al.

(10) Patent No.: US 12,426,869 B2
(45) Date of Patent: Sep. 30, 2025

(54) CONSTANT DISTRACTION FORCE DRIVEN SELF ACTUATING GROWING ROD SYSTEMS

(71) Applicant: Indius Medical Technologies Private Limited, Maharashtra (IN)

(72) Inventors: Aditya Ingalhalikar, Maharashtra (IN); Sagar Sathaye, Maharashtra (IN); Piyali Gokhale, Maharashtra (IN); Dhrumil Shekhda, Gujrat (IN)

(73) Assignee: INDIUS MEDICAL TECHNOLOGIES PRIVATE LIMITED, Pune (IN)

( * ) Notice: Subject to any disclaimer, the term of this patent is extended or adjusted under 35 U.S.C. 154(b) by 58 days.

(21) Appl. No.: 18/441,566

(22) Filed: Feb. 14, 2024

(65) Prior Publication Data
US 2024/0180542 A1 Jun. 6, 2024

Related U.S. Application Data

(63) Continuation-in-part of application No. 18/230,473, filed on Aug. 4, 2023.

(30) Foreign Application Priority Data

Aug. 10, 2022 (IN) .............................. 202221045675

(51) Int. Cl.
A61B 17/02 (2006.01)
A61B 17/00 (2006.01)

(52) U.S. Cl.
CPC .. *A61B 17/025* (2013.01); *A61B 2017/00991* (2013.01); *A61B 2017/0256* (2013.01)

(58) Field of Classification Search
CPC . A61B 17/70; A61B 17/7014; A61B 17/7016; A61B 17/7004; A61B 17/7053; A61B 17/7091; A61B 17/72; A61B 17/7241; A61B 17/86; A61B 17/02
See application file for complete search history.

(56) References Cited

U.S. PATENT DOCUMENTS

| | | | |
|---|---|---|---|
| 8,449,543 | B2 | 5/2013 | Pool et al. |
| 8,961,567 | B2 | 2/2015 | Hunziker |
| 8,974,463 | B2 | 3/2015 | Pool et al. |
| 9,044,281 | B2 | 6/2015 | Pool et al. |

(Continued)

*Primary Examiner* — Christopher J Beccia
(74) *Attorney, Agent, or Firm* — Foley & Lardner LLP

(57) ABSTRACT

A constant distraction force driven self-actuating growing rod system is provided for implantation on a corrected bony anatomy. The system includes components selected from the group consisting of at least one static rod, intermediate rod, or growth rod component; at least one compression spring component; at least one magnetic field-based spring actuation mechanism; at least one mechanical biasing mechanism, at least one casing, at least one guide rod and at least one spring actuator mechanism to apply an active distraction force; at least one magnetic field-based spring actuation mechanism and at least one dynamic sealing plug. During natural growth of the corrected bony anatomy, the growth rod component telescopes out of the intermediate rod component, creating a distraction force deficit that is corrected by causing the compression spring component to get compressed by the magnetic field-based spring actuation mechanism or the mechanical biasing mechanism, thereby maintaining an active distraction force.

18 Claims, 19 Drawing Sheets

(56) References Cited

U.S. PATENT DOCUMENTS

| | | |
|---|---|---|
| 9,060,810 B2 | 6/2015 | Kercher et al. |
| 9,179,960 B2 | 11/2015 | Walker et al. |
| 9,393,119 B2 | 7/2016 | Pool et al. |
| 10,363,069 B2 | 7/2019 | Simpson et al. |
| 10,595,902 B2 | 3/2020 | Ingalhalikar et al. |
| 2015/0134008 A1 | 5/2015 | Kiester |

CONSTANT DISTRACTION FORCE DRIVEN SELF ACTUATING GROWING ROD SYSTEMS

CROSS-REFERENCE TO RELATED PATENT APPLICATIONS

This application is a Continuation-In-Part of U.S. application Ser. No. 18/230,473, filed Aug. 4, 2023, which is a Paris Convention Application claiming priority to Indian Application No. 202221045675 filed Aug. 10, 2022, all of which are incorporated herein by reference in their entireties.

FIELD OF THE INVENTION

The present disclosure relates to medical implants. More particularly, the present disclosure relates to constant distraction force driven self-actuating growing rod systems, to be used as medical implants.

BACKGROUND

A common form of treatment for skeletal deformities is manual correction of the deformity by a surgeon, followed by affixation of medical implants onto the now-corrected bony anatomy, which continues to support the corrected bony anatomy. However, most of the currently existing implant systems support the corrected bony anatomy only till the point up to which natural growth occurs. Every time the patient undergoes natural growth, for instance, elongation of the spine, a surgeon has to cut open the patient and perform manual distraction of the medical implant to match the natural growth. Therefore, these systems are not natural growth driven and are highly invasive. It is crucial to note that it is the surgeon/practitioner who decides how much the system is to be distracted post implantation, and therefore, instances of human error are also inevitable.

There are certain systems that are natural growth-friendly, without the need for surgical intervention. However, such systems are fluid-based and require extra measures such as seals to mitigate the chance of fluid leakage, which increases the overall weight and cost of the system. Furthermore, if the fluid leaks, the distraction force is lost. Furthermore, growth friendly fluid-based designs of the prior art are necessarily accompanied by minimally invasive procedures to increase the distraction force provided by the system as the patient grows.

The inventors of the present disclosure have envisaged a constant distraction force driven self-actuating growing rod system which mitigates the drawbacks of existing systems of the prior art.

OBJECTS

It is an object of the present disclosure to provide a constant distraction force driven self-actuating growing rod system.

It is another object of the present disclosure to provide a constant distraction force driven self-actuating growing rod system for orthopedic deformity correction.

It is yet another object of the present disclosure to provide a constant distraction force driven self-actuating growing rod system which is safe.

It is yet another object of the present disclosure to provide a constant distraction force driven self-actuating growing rod system which is economical.

It is still another object of the present disclosure to provide a constant distraction force driven self-actuating growing rod system which mitigates or eliminates the need for repetitive surgical interventions.

SUMMARY OF THE INVENTION

The present disclosure provides a constant distraction force driven self-actuating growing rod system for implantation on a corrected bony anatomy; said system comprises a combination of components selected from the group consisting of at least one static rod component; at least one intermediate rod component; at least one growth rod component; at least one compression spring component; at least one magnetic field-based spring actuation mechanism; at least one mechanical biasing mechanism, at least one casing, at least one guide rod and at least one spring actuator mechanism adapted to apply an active distraction force onto the system of the present disclosure; at least one magnetic field-based spring actuation mechanism; and at least one dynamic sealing plug. During the natural growth of the corrected bony anatomy, the growth rod component telescopes out of the intermediate rod component, causing the pre-compressed compression spring(s) to relax; creating a distraction force deficit in the system; said distraction force deficit being corrected by causing the relaxed compression spring(s) to regain compression by means of at least one mechanism selected from the group consisting of said magnetic field-based spring actuation mechanism and the mechanical biasing mechanism; thereby maintaining an active distraction force onto the system.

BRIEF DESCRIPTION OF THE ACCOMPANYING DRAWINGS

The present disclosure is illustrated in the accompanying non-limiting drawings, throughout which reference letters indicate corresponding parts in the various figures.

DESCRIPTION

Figure 1:
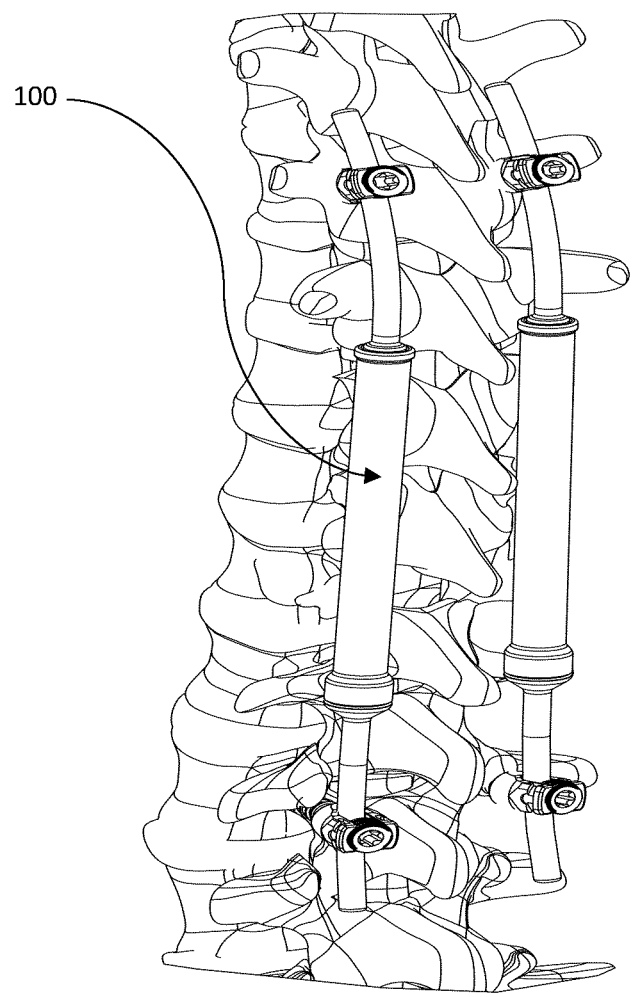
FIG. 1 illustrates a non-limiting embodiment of the constant distraction force driven self-actuating growing rod system (100) of the present disclosure.

The present disclosure provides a constant distraction force driven self-actuating growing rod system (100) for implantation on a corrected bony anatomy, as illustrated in FIG. 1. FIGS. 2-19 illustrate different embodiments of the system (100) with its sub-components and their characteristic construction.

The system (100) of the present disclosure comprises a combination of components selected from the group consisting of at least one static rod component (10); at least one intermediate rod component (20); at least one growth rod component (30); at least one compression spring component (40); at least one magnetic field-based spring actuation mechanism (50) and at least one dynamic sealing plug (60), at least one mechanical biasing mechanism, at least one casing, at least one guide rod and at least one spring actuator mechanism as the major components. The system of the present disclosure also comprises at least one anti-rotation feature selected from the group consisting of gears, splines, keys and ratchet. The present system (100) is designed for the correction of orthopaedic deformities. In one embodiment, the present system (100) is designed for the correction of deformities in the spine.

The basic functioning of the present system (100) is described herein below. Before implanting the system of the present disclosure in the body of a patient needing correction of a skeletal deformity, a surgeon manually corrects the deformity and immediately affixes the system onto the thus-corrected bony anatomy. For the purpose of the present disclosure, the term 'corrected bony anatomy' is to be interpreted to mean the bony anatomy that was originally deformed, but was manually corrected by a surgeon, just prior to implantation of the growing rod system of the present disclosure. The compression spring used in the system of the present disclosure is pre-compressed and therefore applies an active distraction force which continues to support the bony anatomy in the corrected position. For the purpose of the present disclosure, the term 'pre-compressed' is to be interpreted to mean that the compression spring is installed in a way that it always exerts a certain force and is never in a free state. Additionally, when the compression spring component (40) is installed in a pre-compressed state, the total length of the compression spring component is less than the free length. However, during the natural growth of the patient, the growth rod component telescopes out of the intermediate rod component, which houses the spring; thereby relaxing the pre-compressed compression spring leading to a distraction force deficit in the system. The distraction force deficit is corrected by causing the compression spring component to regain compression by at least one mechanism selected from the group consisting of magnetic field-based spring actuation mechanism and the mechanical biasing mechanism; thereby maintaining an active distraction force onto the system. Therefore, the system of the present embodiment continues to support the corrected bony anatomy even throughout the natural growth of the patient. The present system (100) further comprises at least one anti-rotation feature selected from the group consisting of gears, splines, keys, ratchet, or any other suitable mechanism.

Figure 2:
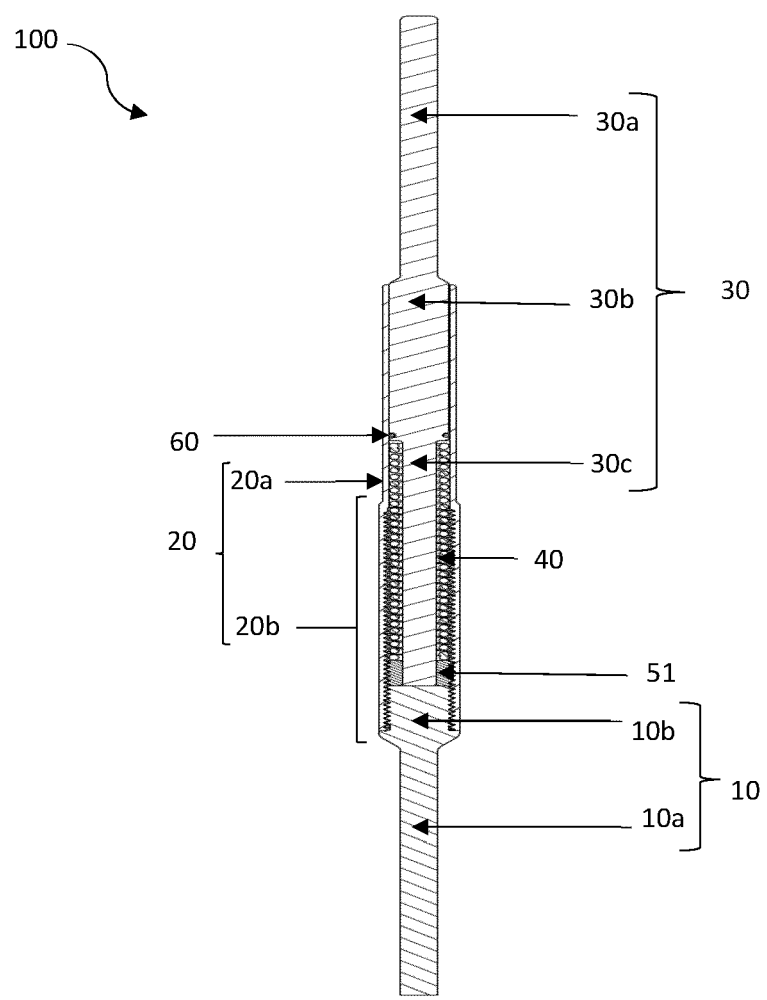
FIG. 2 illustrates a first embodiment of the constant distraction force driven self-actuating growing rod system (100) of the present disclosure at installation, wherein the growth rod component (30) is at zero distraction and the compression spring component (40) is in a pre-compressed state.
Figure 3:
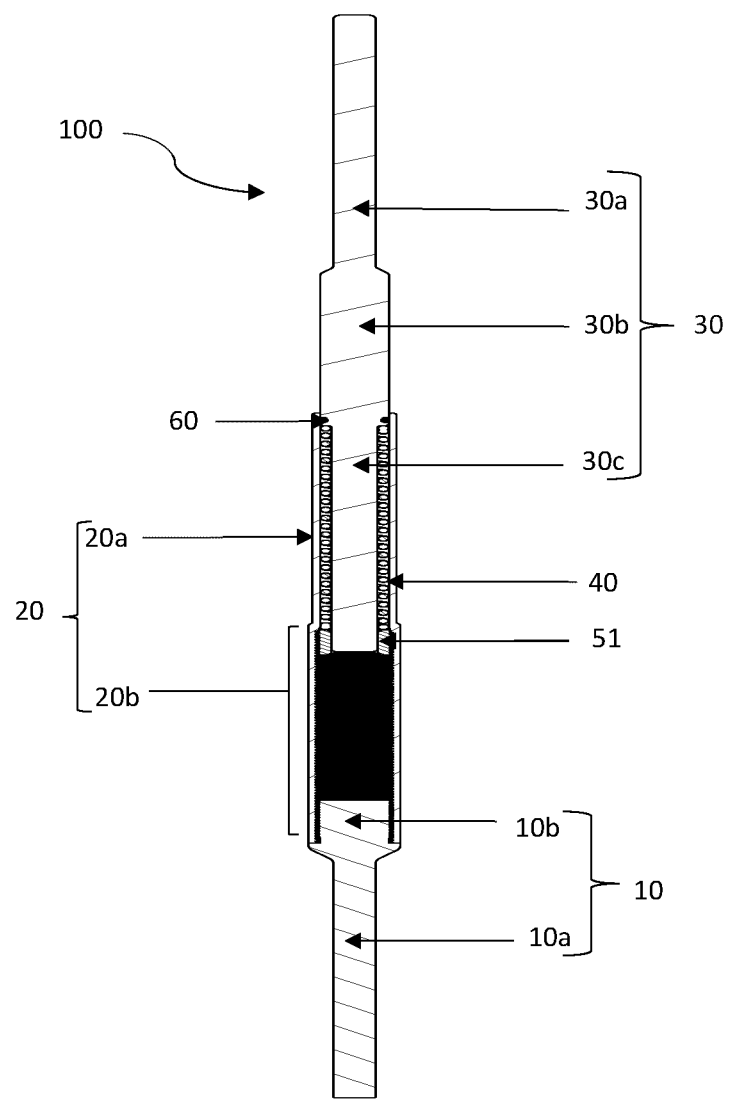
FIG. 3 illustrates the first embodiment of the constant distraction force driven self-actuating growing rod system (100) of the present disclosure pursuant to the natural growth of the corrected bony anatomy, wherein the growth rod component (30) is extended and the compression spring component (40) is compressed.

A first embodiment of the present system (100), as illustrated in FIGS. 2 and 3, is described herein below. In accordance with the first embodiment, the present disclosure provides a constant distraction force driven self-actuating growing rod system (100) comprising at least one static rod component (10); at least one hollow intermediate rod component (20); at least one growth rod component (30); at least one compression spring component (40); at least one magnetic field-based spring actuation mechanism (50) and at least one dynamic sealing plug (60).

The static rod component (10) of the first embodiment comprises a first static segment (10a) and a second static segment (10b). The first static segment (10a) is adapted to be affixed to at least one corrected bony anatomy at a first pre-determined location, which is below the deformity site. The first static segment is affixed by at least one fixation element selected from the group consisting of screw(s), hook(s), band(s), wire(s), connector(s), plate(s), staple(s) or any other fixation element typically used in orthopedic surgery. The second static segment (10b) is threaded along the external circumference and is adapted to couple threadedly with the intermediate rod component (20). The threaded coupling is supplemented by welding.

The hollow intermediate rod component (20) of the first embodiment comprises a first intermediate segment (20a) and a second intermediate segment (20b). The second intermediate segment (20b) is threaded along the internal circumference and is adapted to regulate the upward movement of the magnetic spring actuator component (51) and also facilitate threaded coupling with the second static segment (10b) of the static rod component (10). The hollow intermediate rod component (20) is affixed to the static rod component (10) by threaded coupling and welding such that after such affixation, the intermediate rod component (20) can't rotate with respect to the static rod component (10). In one embodiment, the hollow intermediate rod component (20) is adapted to house the compression spring component (40), the magnetic spring actuator component (51) and the growth rod component (30).

The growth rod component (30) of the first embodiment comprises a first growth segment (30a), a second growth segment (30b) and a third growth segment (30c). The first growth segment (30a) is adapted to be affixed to at least one corrected bony anatomy at a second pre-determined location, which is above the deformity site. The first growth segment is affixed by at least one fixation element selected from the group consisting of screw(s), hook(s), band(s), wire(s), connector(s), plate(s), staple(s) or any other fixation element typically used in orthopedic surgery. The second (30b) and third (30c) growth segments are disposed within the intermediate rod component (20) and configured to telescope out thereof pursuant to the natural growth of the corrected bony anatomy. The growth rod component (30) is connected to the intermediate rod component (20) through a cylindrical joint which allows the motion of the growth rod component (30) with respect to the intermediate rod component (20).

The compression spring component (40) of the first embodiment comprises one compression spring (40) that is coaxially disposed within the intermediate rod component (20), around the third growth segment (30c) of the growth rod component (30) in a pre-compressed state (illustrated in FIG. 2) and sandwiched between the second growth segment (30b) of the growth rod component (30) on a first side and the magnetic spring actuator component (51) on a second side. Since the compression spring component (40) is installed in the system (100) in a pre-compressed state, it is adapted to apply an active distraction force onto the system (100) of the present disclosure, right from the time when the surgeon manually corrects the deformity, followed by affixing the present system (100) onto the corrected bony anatomy. Typically, the compression spring component (40) is at least one selected from the group consisting of a helical coil spring, a conical coil spring, a leaf spring, a constant force spring, a disc spring, a constant rate spring, an extension coil spring and a constant torque spring.

The magnetic field-based spring actuation mechanism (50) of the first embodiment comprises at least one magnetic spring actuator component (51) and at least one magnetic field generating component (not shown in the figures).

The magnetic spring actuator component (51) is threaded along the external circumference and is disposed within the hollow portion of the intermediate rod component (20) in the second intermediate segment (20b), such that one end of the compression spring component (40) rests thereon. The magnetic spring actuator component (51) is adapted to move in at least one motion selected from the group consisting of rotational motion and translational motion. Further, the direction of rotation of the magnetic spring actuator component (51) determines whether the compression spring component (40) gets compressed or relaxed. In one embodiment, the magnetic spring actuator component (51) is adapted to compress the compression spring component (40) upon rotating in a clockwise direction. In another embodiment, the magnetic spring actuator component (51) is adapted to release or cause the compression spring component (40) to relax upon rotating in an anti-clockwise direction.

The magnetic field generating component is located outside the body. The magnetic field generating component is adapted to influence the movement of the magnetic spring actuator component (51) when placed on the back of the patient in contact with skin where the present system (100) is affixed; which in turn compresses the compression spring (41); thereby reinstating the distraction force.

The dynamic sealing plug (60) is affixed between the inner circumference of the first intermediate segment (20a) of the intermediate rod component (20) and the outer circumference of the second growth segment (30b) of the growth rod component (30) and is adapted to prevent movement of at least one contaminant in and out of the system (100). The dynamic sealing plug (60) is at least one selected from the group consisting of O-ring(s), lip seal(s), quad seal(s) or any suitable seals that suit the present application.

During the natural growth of the corrected bony anatomy, the growth rod component (30) telescopes out of the intermediate rod component (20), causing the pre-compressed compression spring (40) to relax; thereby creating a distraction force deficit in the system (100). The distraction force deficit is corrected by causing the relaxed compression spring (40) to get regain compression (illustrated in FIG. 3) by means of the magnetic spring actuator component (51), under the stimulus of magnetic field generating component. The magnetic field generating component causes the magnetic spring actuator component (51) to rotate upwards along the longitudinal axis and along the internal threading of the hollow second intermediate segment (20b) thereby compressing the spring (40) and reinstating an active distraction force onto the system (100).

In post-operative follow ups, a surgeon will take an x-ray of the corrected bony anatomy to determine how much growth has occurred. If the surgeon feels the need to increase the constant distraction force, he will perform a non-invasive procedure, by placing the magnetic field generating component on the back of the patient in contact with skin where the system (100) has been affixed. The magnetic field generating component moves the magnetic spring actuator component (51) that compresses the spring (41); thereby increasing and reinstating the distraction force.

Figure 4:
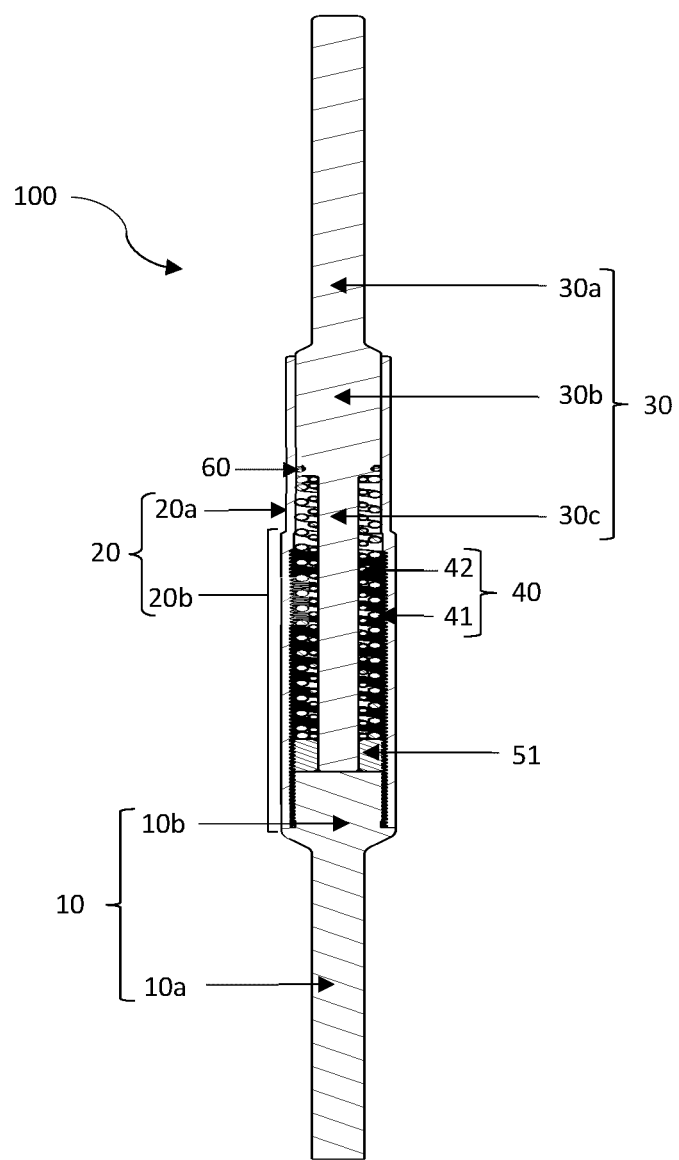
FIG. 4 illustrates a second embodiment of the constant distraction force driven self-actuating growing rod system (100) of the present disclosure at installation, wherein the growth rod component (30) is at zero distraction, the first compression spring (41) is in a pre-compressed state and the second compression spring (42) is in a free state.
Figure 5:
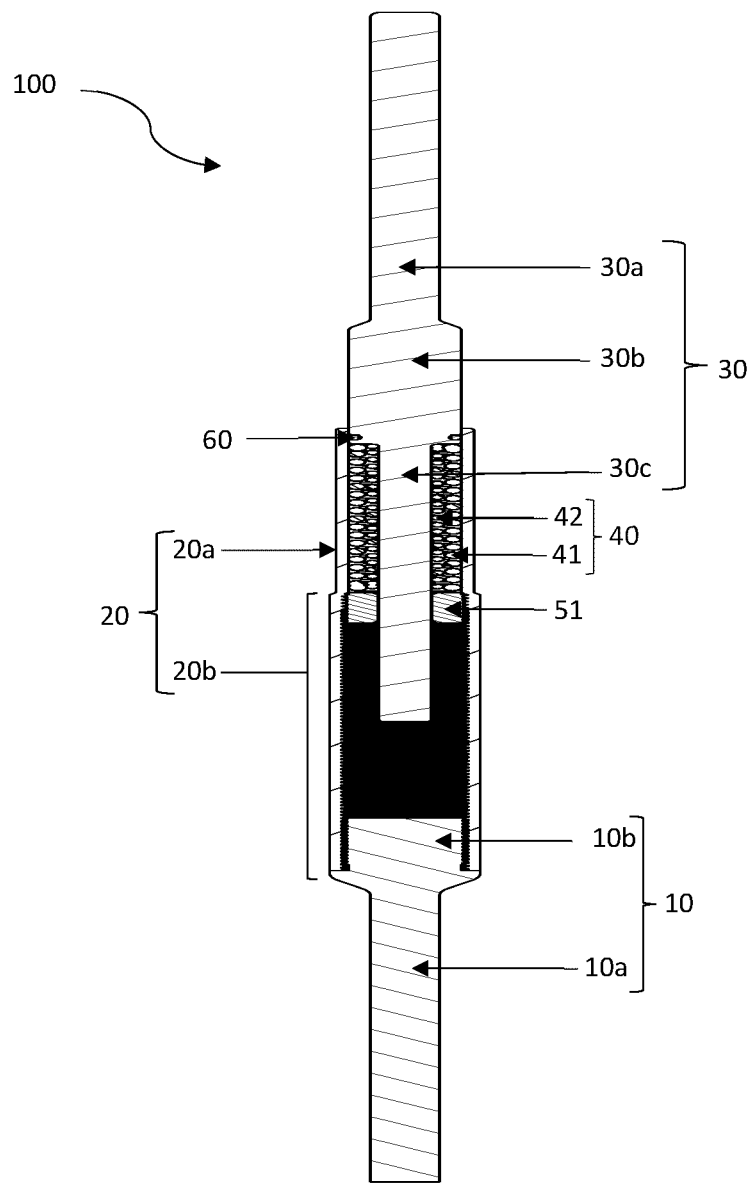
FIG. 5 illustrates a second embodiment of the constant distraction force driven self-actuating growing rod system (100) of the present disclosure pursuant to the natural growth of the corrected bony anatomy, wherein the growth rod component (30) is extended, and the first compression spring (41) is compressed and the second compression spring (42) is also in a compressed state.

In a second embodiment, as illustrated in FIGS. 4 and 5, the present system (100) comprises the same components, construction, and functioning, except for the compression spring component (40). In a second embodiment, the present system (100) comprises two compression springs (41,42) that are coaxially disposed within the hollow portion of the intermediate rod component (20), around the third growth segment (30*c*) of the growth rod component (30) and sandwiched between the second growth segment (30*b*) of the growth rod component (30) on a first side and at least one magnetic spring actuator component (51) at a second side. Typically, the compression spring component (40) is at least one selected from the group consisting of a helical coil spring, a conical coil spring, a leaf spring, a constant force spring, a disc spring, a constant rate spring, an extension coil spring and a constant torque spring.

Typically, the first (41) of the two compression springs has a diameter larger than the diameter of the second (42) of the two compression springs and there is radial clearance therebetween which facilitates the springs (41,42) to work in parallel. At installation, the first (41) of the two compression springs is in a pre-compressed state and the second (42) of the two compression springs is in a free state (illustrated in FIG. 4). At installation the second spring (42) is free, because the required force is provided by the first spring (41) singularly. During implantation of the system (100) disclosed in the second embodiment, the first spring (41) is pre-compressed to provide initial distraction force. After certain growth of the spine, the growing rod component (30) extends from its installation position, causing the pre-compressed spring to relax, which leads to reduction in the distraction force. Hence to re-instate the distraction force, the first compression spring (41) is made to regain compression. This is achieved by rotating the magnetic spring actuator component (51) in the clock-wise direction. To cater to the requirement of maintaining additional distraction force, consequent to additional growth of the spine, which the first spring (41) alone can't balance out, the second spring (42) is included in the system (100). The purpose of inclusion of the second spring (42) in addition to the first (41), is to provide further additional force within the same sized cylinder which is the growing rod system (100), wherein the second compression spring (41) is also compressed by rotating the magnetic spring actuator component (51) in the clock-wise direction (illustrated in FIG. 5).

Figure 6:
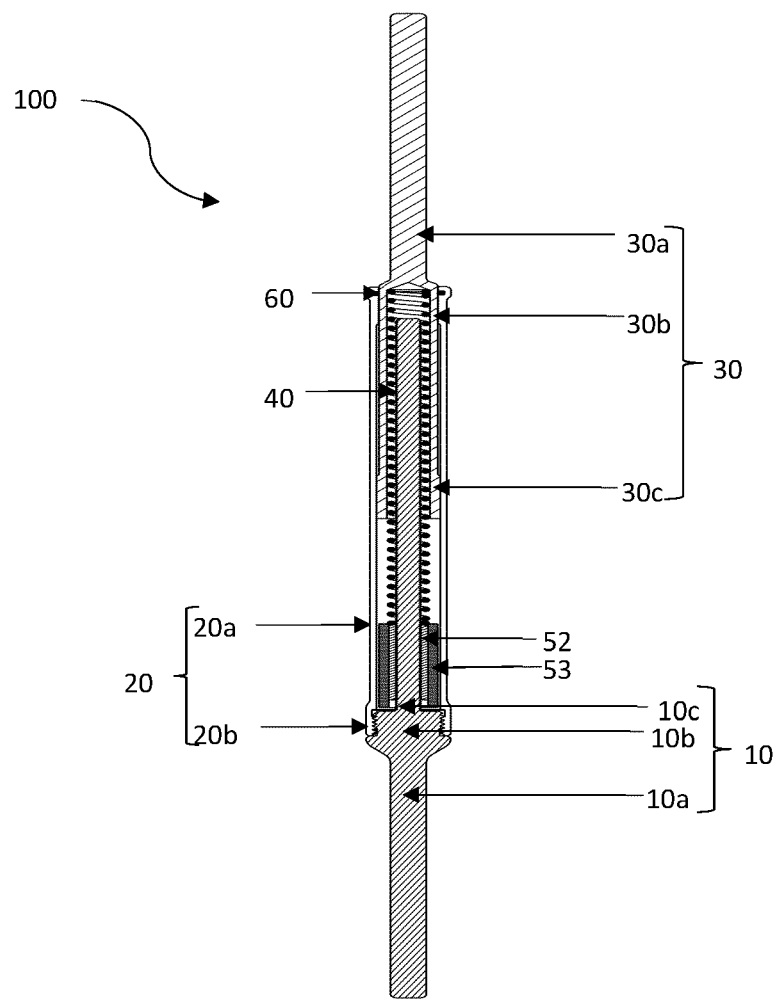
FIG. 6 illustrates a third embodiment of the constant distraction force driven self-actuating growing rod system (100) of the present disclosure at installation, wherein the growth rod component is at zero distraction and the compression spring component (40) is in a pre-compressed state.
Figure 7:
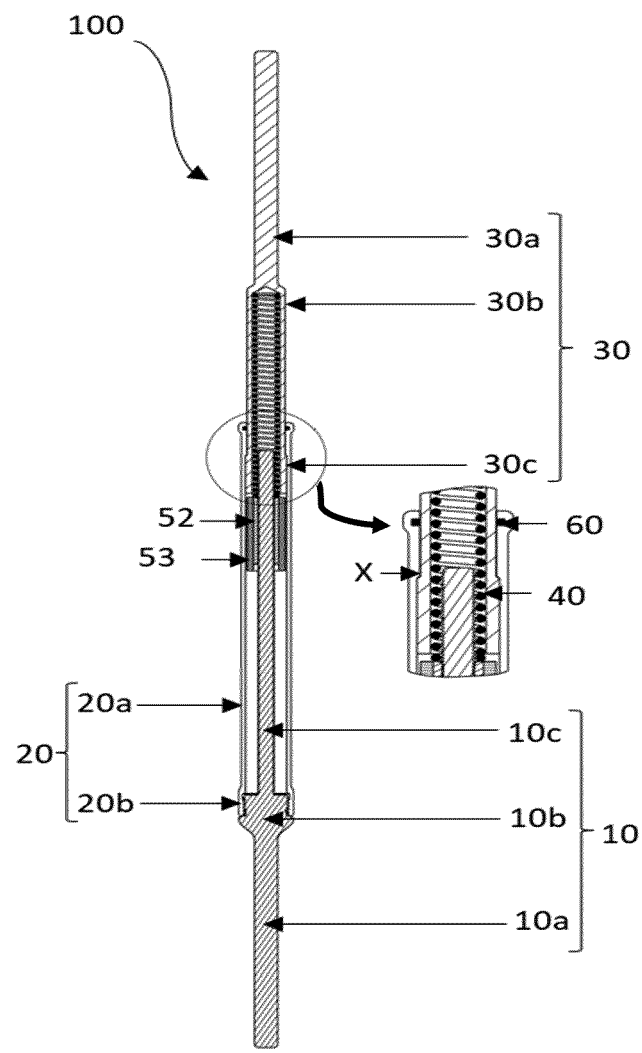
FIG. 7 illustrates the third embodiment of the constant distraction force driven self-actuating growing rod system (100) of the present disclosure pursuant to the natural growth of the corrected bony anatomy, wherein the growth rod component (30) is extended, and the compression spring component (40) is compressed.

A third embodiment of the system (100), as illustrated in FIGS. 6 and 7 comprises at least one static rod component (10), at least one hollow intermediate rod component (20), at least one growth rod component (30), at least one compression spring component (40), at least one magnetic field-based spring actuation mechanism (50) and at least one dynamic sealing plug (60).

The static rod component (10) of the third embodiment is partially threaded along the external circumference and comprises a first static segment (10*a*) and a second static segment (10*b*) and a third static segment (10*c*). The first static segment (10*a*) is adapted to be affixed to at least one corrected bony anatomy at a first pre-determined location, which is below the deformity site. The first static segment is affixed by at least one fixation element selected from the group consisting of screw(s), hook(s), band(s), wire(s), connector(s), plate(s), staple(s) or any other fixation element typically used in orthopedic surgery. The second static segment (10*b*) is threaded along the external circumference and is adapted to couple threadedly with the intermediate rod component (20), followed by welding, which ensures that the intermediate rod component (20) doesn't rotate with respect to the static rod component (10). The third static segment (10*c*) is threaded along the external circumference and is adapted to regulate the upward movement of the spring actuator component (52).

The hollow intermediate rod component (20) of the third embodiment is threadedly coupled with the static rod component (10) and adapted to house the compression spring component (40), the spring actuator component (52), at least one magnetic component (53) and the growth rod component (30). The hollow intermediate rod component (20) comprises a first intermediate segment (20*a*) and a second intermediate segment (20*b*). The second intermediate segment (20*b*) is threaded along the internal circumference and is adapted to threadedly couple with the second static segment (10*b*) of the static rod component (10), followed by welding.

The growth rod component (30) of the third embodiment, is disposed within the intermediate rod component (20) and is configured to envelope the compression spring component (40) and telescope out of the intermediate rod component (20) pursuant to the natural growth of the corrected bony anatomy. The growth rod component (30) comprises a first growth segment (30*a*) and a second growth segment (30*b*) and a third growth segment (30*c*). The first growth segment (30*a*) is adapted to be affixed to at least one corrected bony anatomy at a second pre-determined location, which is above the deformity site. The first growth segment is adapted to be affixed at a point below the corrected bony anatomy by at least one fixation element selected from the group consisting of screw(s), hook(s), band(s), wire(s), connector(s), plate(s), staple(s) or any other fixation element typically used in orthopedic surgery. The second (30*b*) and third growth segment (30*c*) are disposed within the intermediate rod component (20), are hollow and envelope the compression spring component (40) and are configured to telescope out of the intermediate rod component (20), pursuant to the natural growth of the corrected bony anatomy. The growth rod component (30) is connected to the intermediate rod component (20) through a cylindrical joint which allows the motion of the growth rod component (30) with respect to the intermediate rod component (20).

Characteristically, a part of the internal circumference of the first segment (20*a*) of the intermediate rod component (20) and the external circumference of the third segment (30*c*) of the growth rod component (30) have complementary profiles, that fit perfectly into each other, functioning as a physical stop (X) adapted to limit the growth rod (30) from telescoping completely out of the intermediate rod (20).

The compression spring component (40) of the third embodiment, comprises one compression spring (41) that is coaxially disposed within the intermediate rod component (20), further within the second growth segment (30*b*) of the growth rod component (30); thereby sandwiched between the second growth segment (30*b*) of the growth rod component (30) on a first side and the spring actuator component (52) on a second side, in a pre-compressed state (illustrated in FIG. 6). Since the compression spring component (40) is installed in the system (100) in a pre-compressed state, it is adapted to apply an active distraction force onto the system (100) of the present disclosure, right from the time when the surgeon manually corrects the deformity, followed by affixing the present system (100) onto the corrected bony anatomy. Typically, the compression spring component (40) is at least one selected from the group consisting of a helical coil spring, a conical coil spring, a leaf spring, a constant force spring, a disc spring, a constant rate spring, an extension coil spring and a constant torque spring.

The magnetic field-based spring actuation mechanism (50) of the third embodiment comprises at least one spring actuator component (52), at least one magnetic component (53) and at least one magnetic field generating component (not shown in the figures).

The spring actuator component (52) is disposed within the hollow portion of the intermediate rod component (20) in the first intermediate segment (20a), such that one end of the compression spring component (40) rests on the spring actuator component (52). The spring actuator component (52) has an internal bore and is threaded along the internal circumference and is adapted to move upwards along the longitudinal axis and along the external threading of the static rod component (10), consequent to the movement of the magnetic component (53), under the stimulus of the magnetic field generating component, which compresses the compression spring component (40). The spring actuator component (52) being adapted to move in at least one motion selected from the group consisting of rotational motion and translational motion.

The magnetic component (53) is disposed within the hollow portion of the intermediate rod component (20) in the first intermediate segment (20a) and positioned such that there is an air gap between magnetic component (53) and the and static rod component (10). The magnetic component (53) has an internal bore and is press-fitted with the spring actuator component (52) along the external circumference and is adapted to move in at least one motion selected from the group consisting of rotational motion and translational motion.

Further, the direction of rotation of the magnetic component (53) determines whether the compression spring component (40) gets compressed or extended. In one embodiment, the magnetic component (53) and consequently, the spring actuator component (52) are adapted to compress the compression spring component (40) upon rotating in a clockwise direction. In another embodiment, the magnetic component (53) and consequently, the spring actuator component (52) are adapted to release or cause the compression spring component (40) to relax, upon rotating in an anti-clockwise direction.

The magnetic field generating component is located outside the body. The magnetic field generating component is adapted to influence the movement of the magnetic component (53) and consequently the spring actuator component (52), when placed on the back of the patient in contact with skin where the present system (100) is affixed; which in turn compresses the compression spring (41); thereby reinstating the distraction force.

The dynamic seal (60) is affixed between the inner circumference of the first intermediate segment (20a) of the intermediate rod component (20) and the outer circumference of the second growth segment (30b) of the growth rod component (30) and is adapted to prevent movement of at least one contaminant in and out of the system (100). The dynamic sealing plug (60) is at least one selected from the group consisting of O-ring(s), lip seal(s), quad seal(s) or any suitable seals that suit the present application.

During the natural growth of the corrected bony anatomy, the growth rod component (30) telescopes out of the intermediate rod component (20), causing the pre-compressed compression spring (40) to relax; thereby creating a distraction force deficit in the system (100). The distraction force deficit is corrected by manipulating the magnetic component (53) to cause the spring actuator component (52) to move upwards along the longitudinal axis and along the external threading of the third segment of the static rod component (10c), under the stimulus of the magnetic field generating component; thereby causing the relaxed compression spring component (40) to regain compression (as illustrated in FIG. 7) and reinstate and maintain an active distraction force onto the system (100).

In post-operative follow ups, a surgeon will take an x-ray of the corrected bony anatomy to determine how much growth has occurred. If the surgeon feels the need to increase the constant distraction force, he will perform a non-invasive procedure, by placing the magnetic field generating component on the back of the patient in contact with skin where the system (100) has been affixed. The magnetic field generating component causes the magnetic component (53) and consequently, the spring actuator component (52) to compress the compression spring component (40); thereby increasing and reinstating the distraction force.

Figure 8:
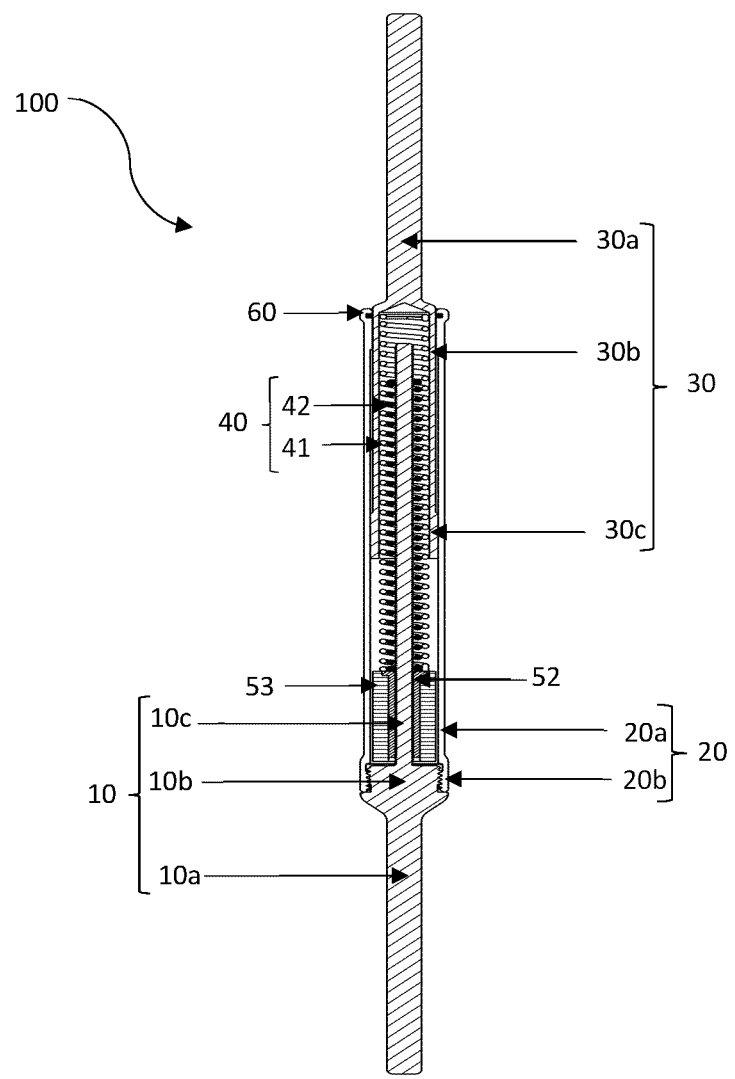
FIG. 8 illustrates a fourth embodiment of the constant distraction force driven self-actuating growing rod system (100) of the present disclosure at installation, wherein the growth rod component (30) is at zero distraction, the first compression spring (41) is in a pre-compressed state and the second compression spring (42) is in a free state.
Figure 9:
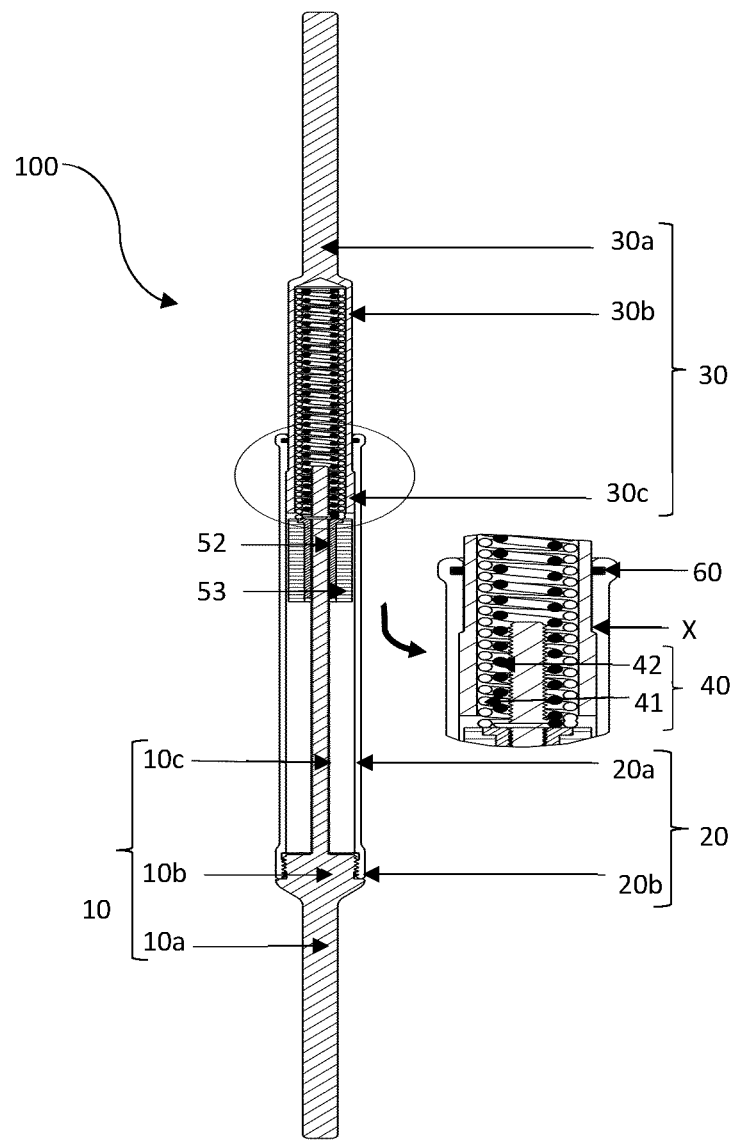
FIG. 9 illustrates a fourth embodiment of the constant distraction force driven self-actuating growing rod system (100) of the present disclosure pursuant to the natural growth of the corrected bony anatomy, wherein the growth rod component (30) is extended, and the first compression spring (41) is compressed, and the second compression spring (42) is also in a compressed state.

In a fourth embodiment, illustrated in FIGS. 8 and 9, the present system (100) comprises the same components, construction and functioning as that of the third embodiment, except for the compression spring component (40). In the fourth embodiment, the present system (100) comprises two compression springs (41,42) that are coaxially disposed within the hollow portion of the intermediate rod component (20), further within the second growth segment (30b) of the growth rod component (30) and sandwiched between the second growth segment (30b) of the growth rod component (30) on a first side and the spring actuator component (52) and the magnetic component (53) at a second side. Typically, the compression spring component (40) is at least one selected from the group consisting of a helical coil spring, a conical coil spring, a leaf spring, a constant force spring, a disc spring, a constant rate spring, an extension coil spring and a constant torque spring.

Typically, the first (41) of the two compression springs (41,42) has a diameter larger than the diameter of the second (42) of the two compression springs (41,42) and there is radial clearance therebetween which facilitates the springs to work in parallel. At installation, the first (41) of the two compression springs is in a pre-compressed state and the second (42) of the two compression springs is in a free state (as illustrated in FIG. 8). At installation the second spring (42) is free, because the required force is provided by the first spring (41) singularly. During implantation of the system (100) disclosed in the fourth embodiment, the first spring (41) is pre-compressed to provide initial distraction force. After certain growth of the spine, the growing rod component (30) extends from its installation position, causing the pre-compressed spring to relax, which leads to reduction in the distraction force. Hence to re-instate the distraction force, the first compression spring (41) is made to regain compression. This is achieved by rotating the magnetic component (53) and the spring actuator component (52) in the clock-wise direction. To cater to the requirement of maintaining additional distraction force, consequent to additional growth of the spine, which the first spring (41) alone can't balance out, the second spring (42) is introduced. The purpose of inclusion of the second spring (42) in addition to the first (41), is to provide further additional force within the same sized cylinder which is the growing rod system (100), wherein the second compression spring (42) is also compressed by rotating the magnetic component (53) and the spring actuator component (52) in the clockwise direction (illustrated in FIG. 9)

Figure 10:
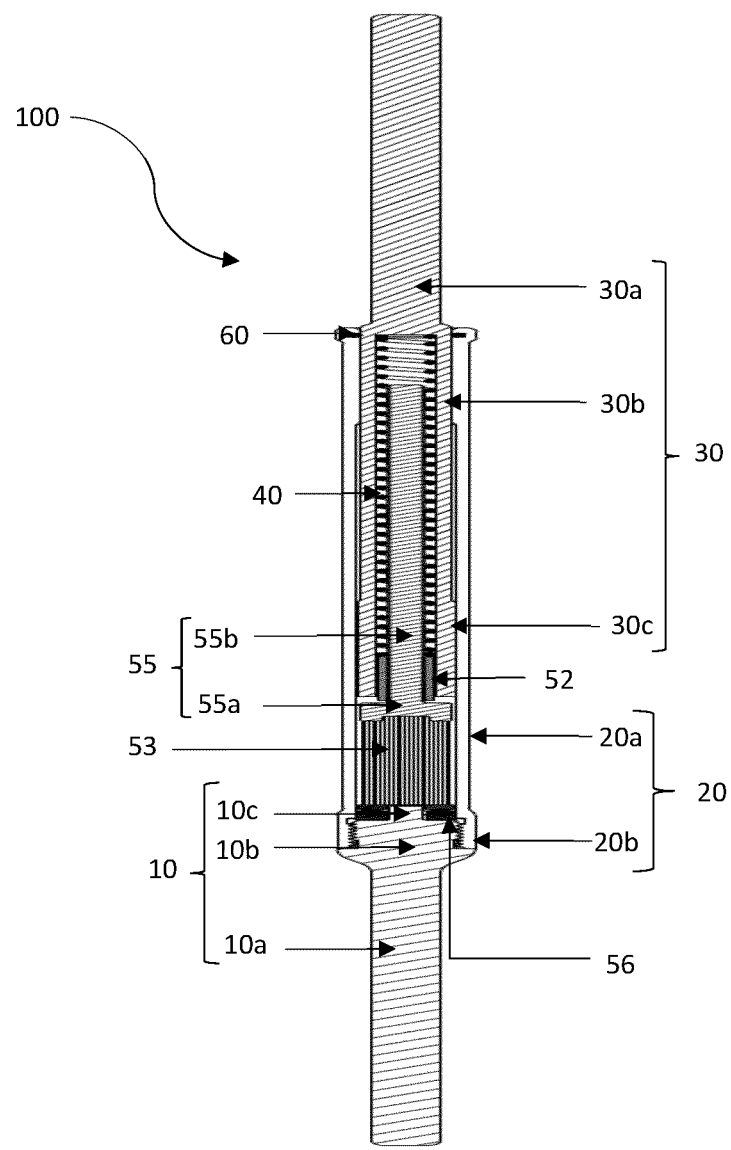
FIG. 10 illustrates a fifth embodiment of the constant distraction force driven self-actuating growing rod system (100) of the present disclosure at installation, wherein the growth rod is at zero distraction and the compression spring component (40) is in a pre-compressed state.
Figure 11:
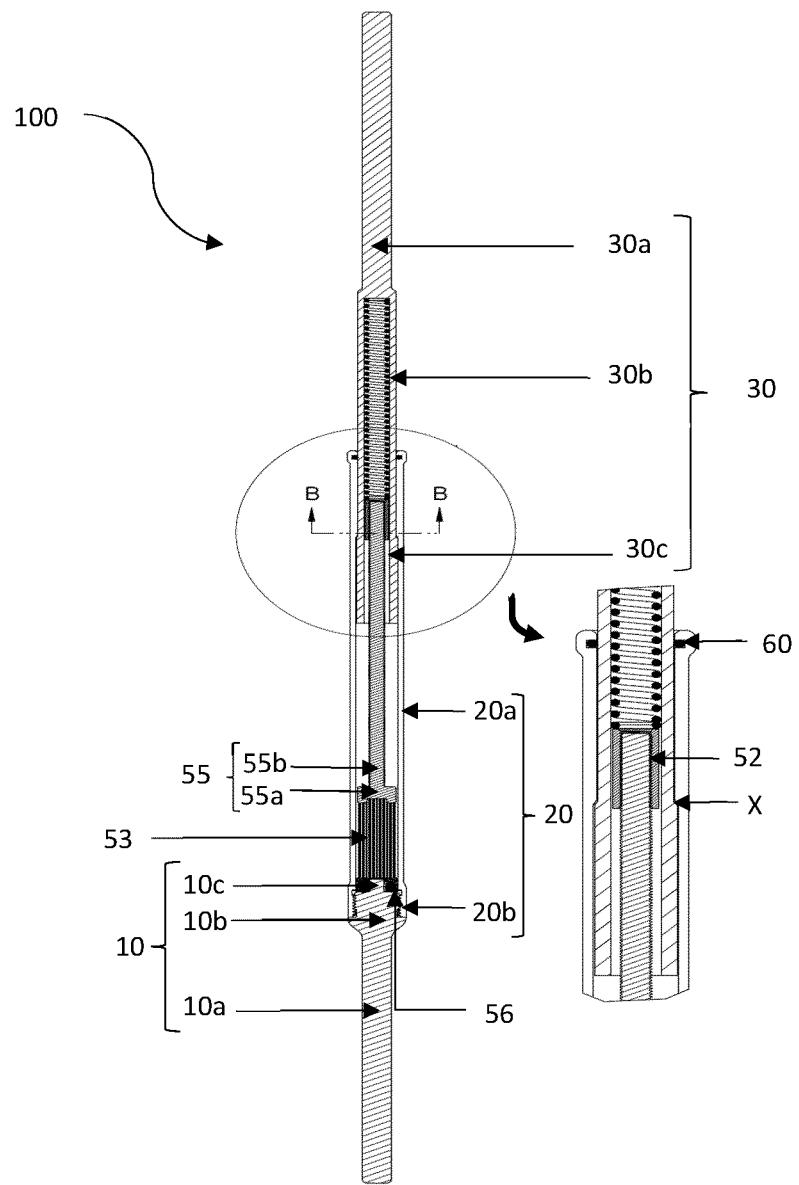
FIG. 11 illustrates a fifth embodiment of the constant distraction force driven self-actuating growing rod system (100) of the present disclosure pursuant to the natural growth of the corrected bony anatomy, wherein the growth rod component (30) is extended, and the compression spring component (40) is compressed.

A fifth embodiment of the present system (100), as illustrated in FIGS. 10 and 11, is described herein below. The fifth embodiment of the present system (100) comprises at least one static rod component (10); at least one hollow intermediate rod component (20), at least one growth rod component (30); at least one compression spring component (40); at least one magnetic field-based spring actuation mechanism (50) and at least one dynamic sealing plug (60). The magnetic field-based spring actuation mechanism (50) of the fifth embodiment comprises at least one spring actuator component (52), at least one magnetic component (53), at least one actuator-magnet connector (55), at least one thrust bearing (56) and at least one magnetic field generating component.

The static rod component (10) of the fifth embodiment comprises a first static segment (10a) and a second static segment (10b) and a third static segment (10c). The first static segment (10a) is adapted to be affixed to at least one corrected bony anatomy at a first pre-determined location, which is below the deformity site. The first static segment is affixed by at least one fixation element selected from the group consisting of screw(s), hook(s), band(s), wire(s), connector(s), plate(s), staple(s) or any other fixation element typically used in orthopedic surgery. The second static segment (10b) is threaded along the external circumference and is adapted to couple threadedly with the intermediate rod component (20) followed by welding, to ensure that the intermediate rod component (20) can't rotate with respect to the static rod component (10). The third static segment (10c) is adapted to be surrounded by at least one thrust bearing (56). The thrust bearing (56) facilitates the smooth rotation of the magnetic component (53).

The intermediate rod component (20) of the fifth embodiment, is threadedly coupled with the static rod component (10) and is adapted to house the compression spring component (40), the spring actuator component (52), the magnetic component (53), the actuator-magnet connector (55) and the growth rod component (30). The hollow intermediate rod component (20) of the fifth embodiment comprises a first intermediate segment (20a) and a second intermediate segment (20b). The second intermediate segment (20b) is threaded along the internal circumference is adapted to threadedly couple with the second static segment (10b) of the static rod component (10).

The growth rod component (30) of the fifth embodiment, is disposed within the intermediate rod component (20) and is configured to envelope the compression spring component (40) and telescope out of the intermediate rod component (20) pursuant to the natural growth of the corrected bony anatomy. The growth rod component (30) comprises a first growth segment (30a), a second growth segment (30b) and a third growth segment (30c). The first growth segment (30a) is adapted to be affixed to at least one corrected bony anatomy at a second pre-determined location, which is above the deformity site. The first growth segment is adapted to be affixed at a point below the corrected bony anatomy by at least one fixation element selected from the group consisting of screw(s), hook(s), band(s), wire(s), connector(s), plate(s), staple(s) or any other fixation element typically used in orthopedic surgery. The second growth segment (30b) is disposed within the intermediate rod component (20), is hollow and envelope the compression spring component (40). Furthermore, the growth rod component has at least one flat profiles (Y) along the internal circumference and is configured to telescope out of the intermediate rod component (20) pursuant to the natural growth of the corrected bony anatomy. The growth rod component (30) is connected to the intermediate rod component (20) through a cylindrical joint which allows the motion of the growth rod component (30) with respect to the intermediate rod component (20).

Characteristically, a part of the internal circumference of the first segment (20a) of the intermediate rod component (20) and the external circumference of the third segment (30c) of the growth rod component (30) have complementary profiles, that fit perfectly into each other, functioning as a physical stop (X) adapted to limit the growth rod (30) from telescoping completely out of the intermediate rod (20).

The compression spring component (40) of the fifth embodiment, comprises one compression spring (40) that is coaxially disposed within the intermediate rod component (20), further within the second growth segment (30b) of the growth rod component (30) and around the actuator-magnet connector (55); thereby sandwiched between the second growth segment (30b) of the growth rod component (30) on a first side and the spring actuator component (52) on a second side, in a pre-compressed state (as illustrated in FIG. 10). Since the compression spring component (40) is installed in the system (100) in a pre-compressed state, it is adapted to apply an active distraction force onto the system (100) of the present disclosure, right from the time when the surgeon manually corrects the deformity, followed by affixing the present system (100) onto the corrected bony anatomy. Typically, the compression spring component (40) is at least one selected from the group consisting of a helical coil spring, a conical coil spring, a leaf spring, a constant force spring, a disc spring, a constant rate spring, an extension coil spring and a constant torque spring.

In the magnetic field-based spring actuation mechanism (50) of the fifth embodiment comprises a spring actuator component (52), a magnetic component (53) and a actuator-magnet connector (55), that are disposed within the hollow portion of the intermediate rod component (20), such that one end of the compression spring component (40) rests on the spring actuator component (52). the magnetic field-based spring actuation mechanism (50) of the present embodiment also comprises a magnetic field generating component (not shown in the figures).

The spring actuator component (52) is disposed within the hollow portion of the intermediate rod component (20) in the first intermediate segment (20a). The spring actuator component (52) has an internal bore and at least one flat profile (Z) along the external circumference and is threaded along the internal circumference. The spring actuator component (52) is adapted to translate upwards along the longitudinal axis and along the external threading of the actuator-magnet connector (55), consequent to the movement of the magnetic component (53), under the stimulus of the magnetic field generating component and compress the relaxed part of compression spring component (40), during natural growth.

Typically, the flat profile (Y) along the internal circumference of the second (30b) and third growth segment (30c) of the growth rod component (30) and the flat profile (Z) along the external circumference of the spring actuator complement (52) are complementary.

The magnetic component (53) is solid and cylindrical and rests on the thrust bearing (56) on one side and is in connection with the actuator-magnetic connector (55) on the other side and is adapted to move in a rotational motion.

The actuator-magnet connector (55) comprises a first actuator-magnet connector segment (55a) and a second actuator-magnet connector segment (55b); wherein the first actuator-magnet connector segment (55a) is in direct contact with the magnetic component (53) and the second actuator-magnet connector segment (55b) is threaded along the external circumference and is adapted to move in a rotational motion and regulate the upward movement of the spring actuator component (52).

Further, the direction of rotation of the magnetic component (53) determines whether the compression spring component (40) gets compressed or relaxed. In one embodiment, the magnetic component (53) and consequently the actuator-magnet connector (55) and the spring actuator component (52) are adapted to compress the compression spring component (40) upon moving in a clockwise direction. In another embodiment, the magnetic component (53) and consequently, the actuator-magnet connector (55) and the spring actuator component (52) are adapted to release or cause the compression spring component (40) to relax, upon rotating in an anti-clockwise direction.

The magnetic field generating component is located outside the body. The magnetic field generating component is adapted to influence the movement of the magnetic component (53) and consequently the spring actuator component (52) and the actuator-magnet connector (55), when placed on the back of the patient in contact with skin where the present system (100) is affixed; which in turn compresses the compression spring (41); thereby reinstating the distraction force.

Figure 14:
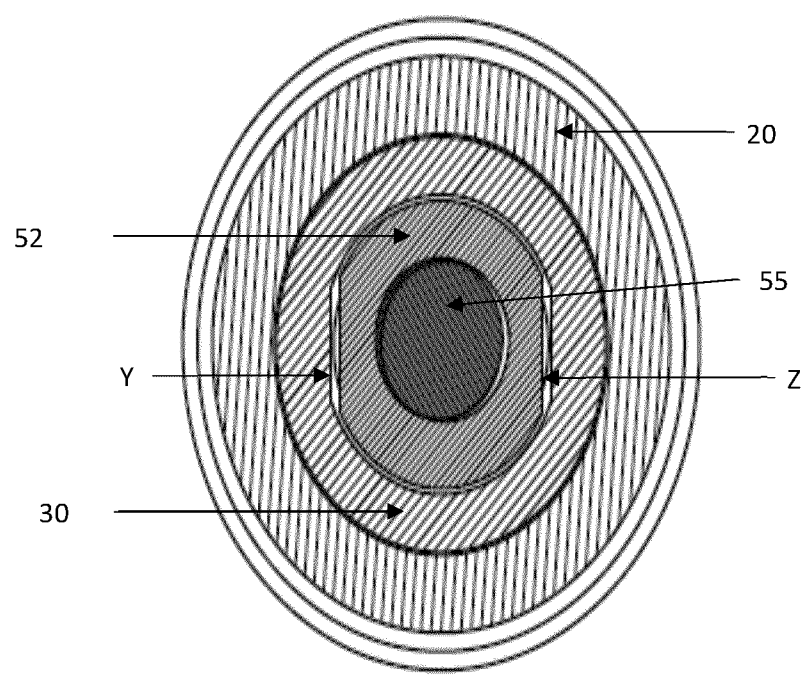
FIG. 14 illustrates a cross sectional view of the fifth and/or sixth embodiment of the constant distraction force driven self-actuating growing rod system (100) of the present disclosure.

There is a flat profile (Z), as illustrated in FIG. 14, along the external circumference of the spring actuator component (52) which complements the flat profile (Y) along the internal circumference of the second (30b) and third growth segment (30c) of the growth rod component (30). The peculiar design of flat profiles will prohibit the spring actuator component (52) to rotate inside the growth rod component (30) upon magnetic induction, thereby allowing only translational motion of the spring actuator component (52).

The dynamic seal (60) is affixed between the inner circumference of the first intermediate segment (20a) of the intermediate rod component (20) and the outer circumference of the second growth segment (30b) of the growth rod component (30) and is adapted to prevent movement of at least one contaminant in and out of the system (100). The dynamic sealing plug (60) is at least one selected from the group consisting of O-ring(s), lip seal(s), quad seal(s) or any suitable seals that suit the present application.

During the natural growth of the corrected bony anatomy, the growth rod component (30) telescopes out of the intermediate rod component (20), causing the pre-compressed compression spring component (40) to relax; thereby creating a distraction force deficit in the system (100). The distraction force deficit is corrected by manipulating the magnetic component (53) to further manipulate the actuator-magnet connector (55) and cause the spring actuator component (52) to move upwards along the longitudinal axis and along the external threading of the actuator-magnet connector (55), under the stimulus of the magnetic field generating component; thereby causing the relaxed compression spring component (40) to regain compression (as illustrated in FIG. 11) and reinstate the active distraction force onto the system (100).

In post-operative follow ups, a surgeon will take an x-ray of the corrected bony anatomy to determine how much growth has occurred. If the surgeon feels the need to increase the constant distraction force, he will perform a non-invasive procedure, by placing the magnetic field generating component on the back of the patient in contact with skin where the system (100) has been affixed. The magnetic field generating component causes the magnetic component (53) and consequently, the spring actuator component (52) to compress the compression spring component (40); thereby increasing and reinstating the distraction force.

Figure 12:
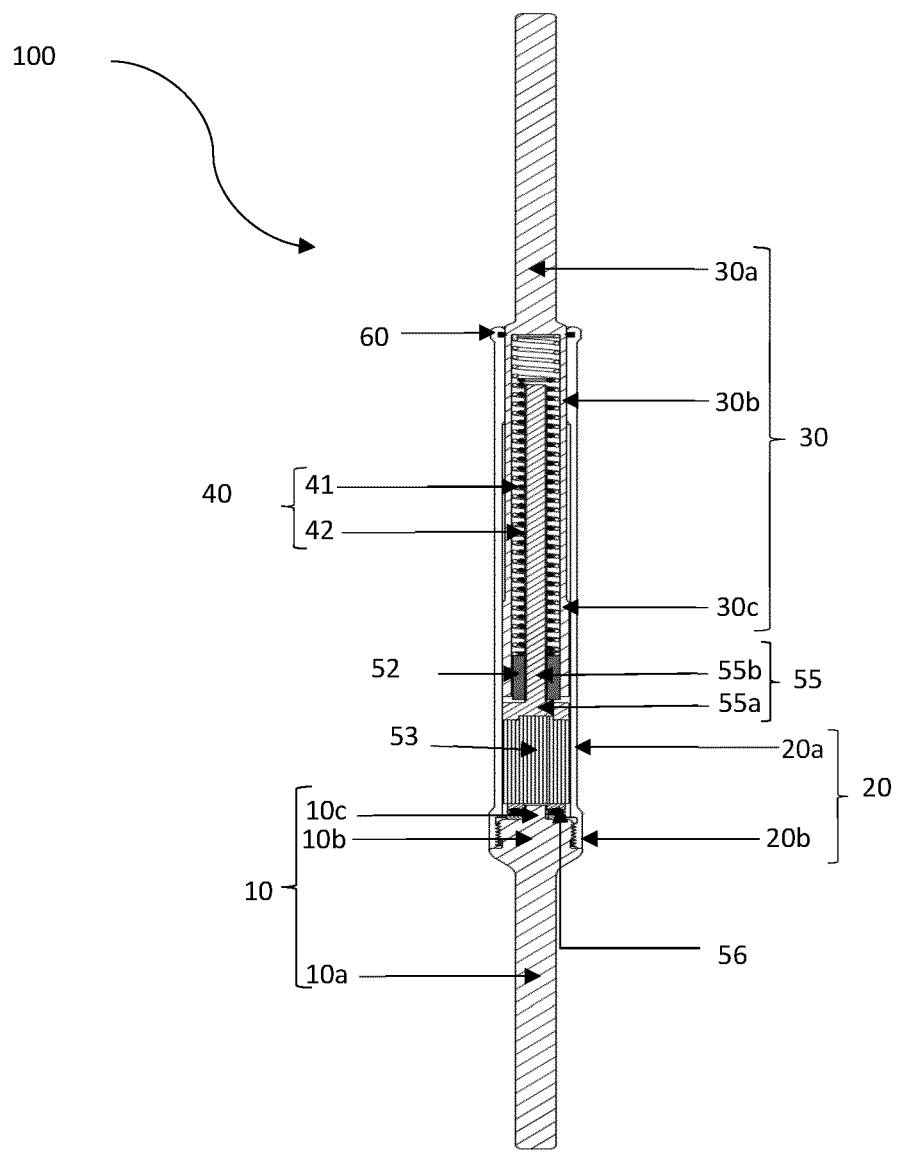
FIG. 12 illustrates a sixth embodiment of the constant distraction force driven self-actuating growing rod system (100) of the present disclosure at installation, wherein the growth rod component (30) is at zero distraction, the first compression spring (41) is in a pre-compressed state and the second compression spring (42) is in a free state.
Figure 13:
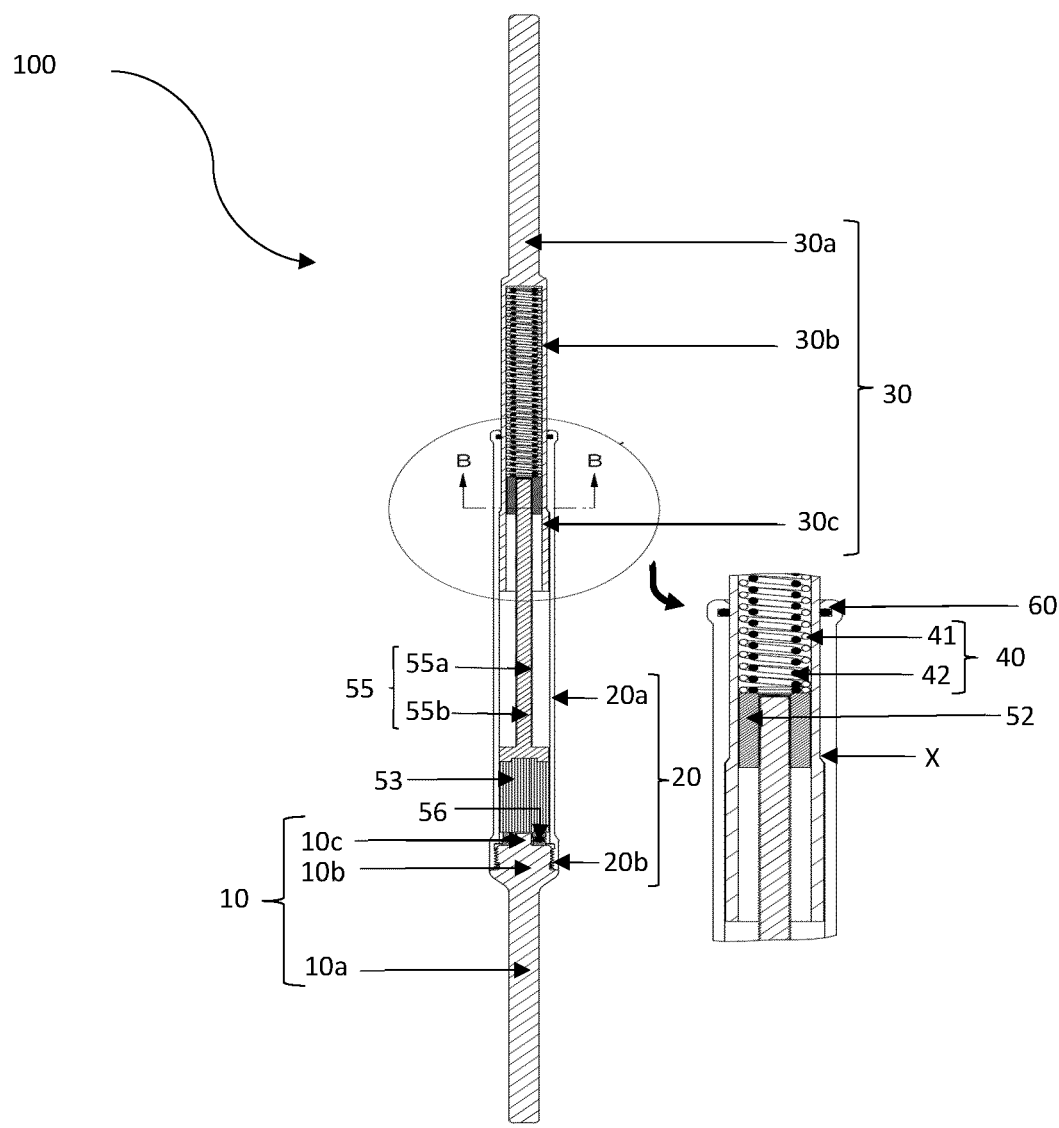
FIG. 13 illustrates a sixth embodiment of the constant distraction force driven self-actuating growing rod system (100) of the present disclosure pursuant to the natural growth of the corrected bony anatomy, wherein the growth rod component (30) is extended, and the first compression spring (41) is compressed, and the second compression spring (42) is also in a compressed state.

In a sixth embodiment, as illustrated in FIGS. 12 and 13, the present system (100) comprises the same components, construction and functioning as that of the fifth embodiment, except for the compression spring component (40). In a sixth embodiment, the present system (100) comprises two compression springs (41,42) that are installed coaxially within the intermediate rod component (20), further within the second growth segment (30b) of the growth rod component (30) and around the actuator-magnet connector (55); thereby sandwiched between the second growth segment (30b) of the growth rod component (30) on a first side and the spring actuator component (52) on a second side. At installation, the first (41) of the two compression springs (41,42) is in a compressed state and the second (42) of the two compression springs (41,42) is in a free state (as illustrated in FIG. 12). Typically, the first (41) of the two compression springs (41,42) has a diameter larger than the diameter of the second (42) of the two compression springs (41,42) and there is radial clearance therebetween which facilitates the springs to work in parallel. Typically, the compression spring component (40) is at least one selected from the group consisting of a helical coil spring, a conical coil spring, a leaf spring, a constant force spring, a disc spring, a constant rate spring, an extension coil spring and a constant torque spring.

During implantation of the system (100) disclosed in the sixth embodiment, the first spring (41) is pre-compressed to provide initial distraction force. After certain growth of the spine, the growing rod component (30) extends from its installation position, causing the pre-compressed spring to relax, which leads to reduction in the distraction force. Hence to re-instate the distraction force, the first compression spring (41) is made to regain compression. This is achieved by rotating the magnetic component (53) and the actuator-magnet connector (55) in the clock-wise direction, resulting in upward translation of spring actuator component (52). To cater to the requirement of maintaining additional distraction force, consequent to additional growth of the spine, which the first spring (41) alone can't balance out, the second spring (42) is introduced. The purpose of inclusion of the second spring (42) in addition to the first (41), is to provide further additional force within the same sized cylinder which is the growing rod system (100) wherein the second compression spring (42) is compressed by rotating the magnetic component (53) and the actuator-magnet connector (55) in the clock-wise direction (illustrated in FIG. 13).

It is crucial to note that multiple other embodiments of the present system (100) are possible by incorporating a plurality of compression spring components (40).

Furthermore, the magnetic field-based spring actuation mechanism (50) may consist of either one of the magnetic spring actuator component (51) or spring actuator component (52) or magnetic component (53) or actuator-magnet connector (55) or one thrust bearing (56) and magnetic field generating component depending on the embodiment considered.

Figure 15:
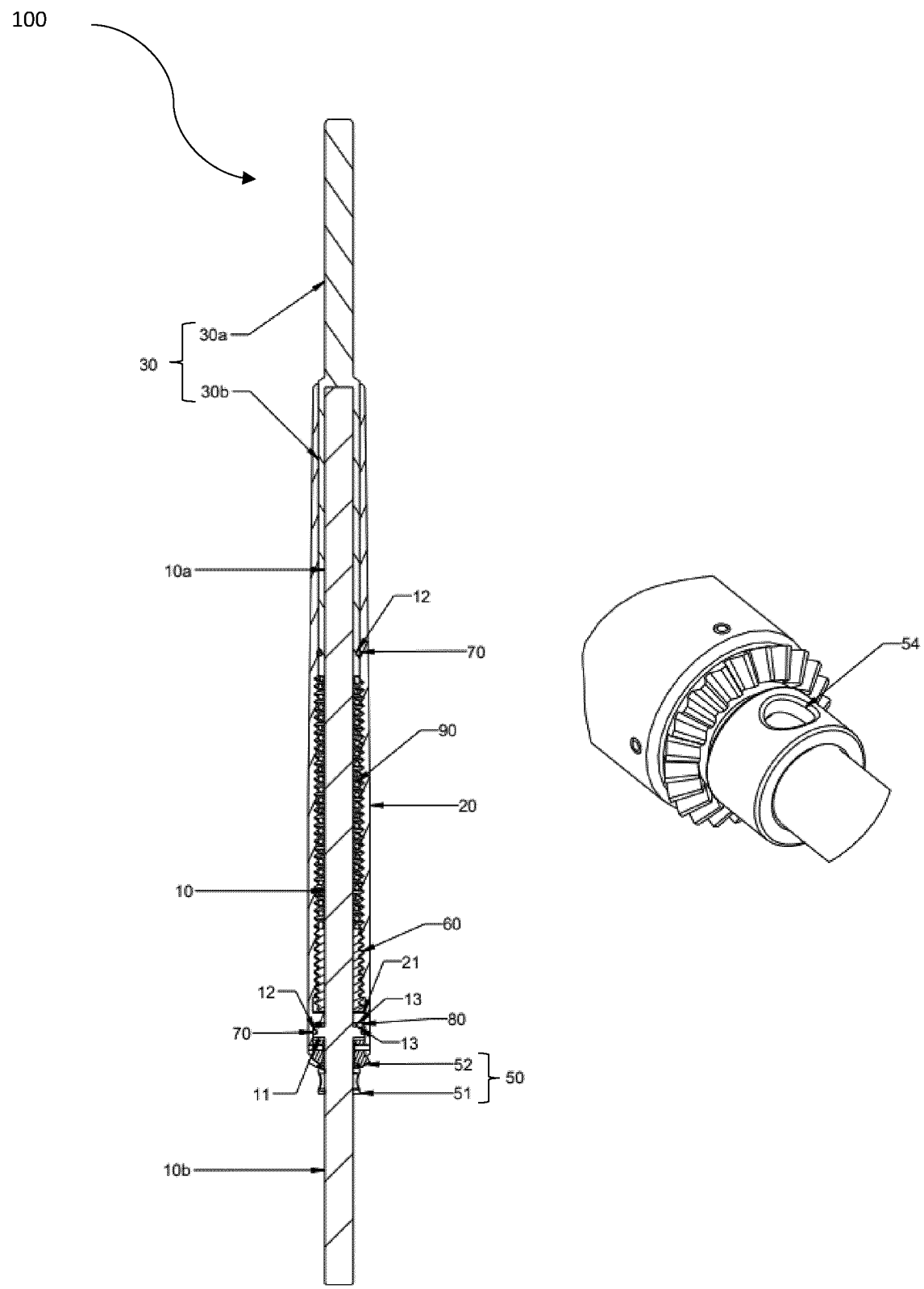
FIG. 15 illustrates a cross sectional view of the seventh embodiment of the constant distraction force driven self-actuating growing rod system (100) of the present disclosure.

A seventh embodiment of the present system (100), as illustrated in FIG. 15, is described herein below. The system of the seventh embodiment comprises at least one static rod component (10); at least one hollow intermediate rod component (20); at least one growth rod component (30); at least one mechanical biasing mechanism (50); at least one spring actuator component (60); at least one dynamic seal plug (70); at least one bearing (80) and at least one compression spring component (90) as the major components.

Before implanting the system (100) of the present embodiment in the body of a patient needing correction of a skeletal deformity, a surgeon manually corrects the deformity and immediately affixes the system (100) onto the now-corrected bony anatomy. The pre-compressed compression spring component (90) that is a part of the system (100) of the present embodiment, applies an active distraction force which continues to support the bony anatomy in the corrected position. However, during the natural growth of the patient, the growth rod component (30) telescopes out of the intermediate rod component (20), which relaxes the pre-compressed compression spring (90) leading to a distraction force deficit in the system (100). The distraction force deficit is corrected by causing the compression spring component (90) to regain compression by the mechanical biasing mechanism (50); thereby maintaining an active distraction force onto the system (100). Therefore, the system (100) of the present embodiment continues to support the corrected bony anatomy even throughout the natural growth of the patient. In one embodiment, the system (100) of the present embodiment is designed for the correction of deformities in the spine. The detailed construction and working of the system (100) of the present embodiment is provided herein after.

The static rod component (10) of the present embodiment has a varying cross-section along its length and comprises a first static segment (10a) and a second static segment (10b). The first static segment (10a) covers about 60 to 80% of the static rod component (10) and has a non-circular cross section. The second static segment (10b) covers around 20 to 40% of the static rod component (10) and has a circular cross section. There comprises at least one stepped up shoulder (11) at the junction of the first (10a) and second static segment (10b).

The second static segment (10b) of the static rod component (10) is adapted to be affixed at a point below the corrected bony anatomy by at least one fixation element selected from the group consisting of screw(s), hook(s), band(s), wire(s), connector(s), plate(s), staple(s) or any other fixation element typically used in orthopedic surgery.

The entire first static segment (10a) of the static rod component (10), the stepped up shoulder (11) and a small part of the second static segment (10b) are disposed concentrically within the intermediate rod component (20).

On the side of the stepped up shoulder (11), there exists at least one groove (12) to accommodate at least one dynamic seal plug (70). In one embodiment, the dynamic seal plug (70) of the present embodiment is an o-ring. On the proximal face of the stepped up shoulder (11), there exists at least one groove (13) which acts as a seat for at least one bearing (80).

The mechanical biasing mechanism (50) comprises at least one driving gear seat (51), at least one driven gear (52) and at least one driving gear (53) (not shown in figures). The second segment (10b) of the static rod component (10) is adapted to mount the driving gear seat (51) sandwiched between the point of affixation to the corrected bony anatomy and the stepped up shoulder (11). A driven gear (52) is also sandwiched between the point of affixation to the corrected bony anatomy and the stepped up shoulder (11) and is partially disposed inside the intermediate rod component (20). The driven gear (52) is fixedly attached to the intermediate rod component (20) by means of at least one attachment mechanism selected from the group consisting of welding, press-fit, threads, adhesives and connecting pins. In one embodiment, the attachment mechanism of the present embodiment is connecting pins (110). Furthermore, the attachment with the connecting pin(s) (110) is supplemented by welding. The driving gear seat (51) is adjacent to the driven gear (52) and consists of a circular pocket (54) which is adapted to guide at least one driving gear (53) to dock at a particular position with respect to the static rod component (10), such that when the driving gear (53) is docked in the driving gear seat (51) and rotated, the driven gear (52), also rotates. The driving gear seat (51) is located outside the intermediate rod component (10).

The growth rod component (30) of the present embodiment comprises a first solid cylindrical first growth segment (30a) and a hollow cylindrical second growth segment (30b). The solid cylindrical first growth segment (30a) is adapted to be affixed at a point above the corrected bony anatomy by at least one fixation element selected from the group consisting of screw(s), hook(s), band(s), wire(s), connector(s), plate(s), staple(s) or any other fixation element typically used in orthopedic surgery. The hollow cylindrical second growth segment (30b) is partially disposed within the intermediate rod component (20) described herein above and is configured to telescope out thereof pursuant to a natural growth of the corrected bony anatomy. The hollow cylindrical second growth segment (30b) comprises at least one groove (12) on the outer circumference to accommodate at least one dynamic seal plug (70). In one embodiment, the dynamic seal plug (70) of the present embodiment is an o-ring.

The intermediate rod component (20) of the present embodiment is hollow and cylindrical and comprises threads over a substantial part of the longitudinal length of the internal surface. Towards the distal end, the intermediate rod component (20) comprises at least one internal step (21), the proximal surface of which is adapted to house at least one spring actuating component (60) and the distal surface of which comprises at least one groove (13) complementary to the groove on the static rod component (10) to accommodate the bearings (80). Since the driven gear (52) is fixedly attached to the intermediate rod component (20), rotation of the driven gear (52) consequently causes rotation of the intermediate rod component (20).

The spring actuating component (60) of the present embodiment comprises at least one internal bore which enables the spring actuating component (60) to be installed on the static rod component (10) over the non-circular section region, abutting the internal step (21) of the intermediate rod component (20). The spring actuating component (60) has external threading over its outer circumference which enables the spring actuating component (60) to ride over the threads of the intermediate rod component (20).

The compression spring component (90) of the present embodiment comprises at least one compression spring that is coaxially disposed within the hollow intermediate rod component (20). The compression spring component (90) abuts the hollow cylindrical second growth segment (30b) of the growth rod component (30) at a first end and rests on the spring actuating component (60) a second end. The compression spring component (90) is installed in the system (100) of the present disclosure in a pre-compressed state and is adapted to apply an active distraction force onto the system (100). The compression spring component (90) of the present disclosure is at least one selected from the group consisting of a helical coil spring, a conical coil spring, a leaf spring, a constant force spring, a disc spring, a constant rate spring, an extension coil spring and a constant torque spring.

The bearings (80) are installed at the interfacing point of the intermediate rod component (20) and the stepped up shoulder (11) of the static rod component (10) to facilitate smooth rotation of the intermediate rod component (20).

During the natural growth of the corrected bony anatomy, as the distraction force deficit gets created, a surgeon performs a minimally invasive surgery where they manually insert a driving gear (53) and dock it into the driving gear seat (51). Since the driving gear (52) perfectly mates with the driven gear (52), the resulting mechanical connection causes the intermediate rod component (20) to rotate, when driving gear (53) is rotated by the surgeon. Due to the rotation of the intermediate rod component (20), the spring actuator component (60) translates upwards as the compression spring component (90) and the intermediate rod component (20) are threadedly connected, resulting in compression of the compression spring component (90), resulting in increase in the distraction force.

Figure 16:
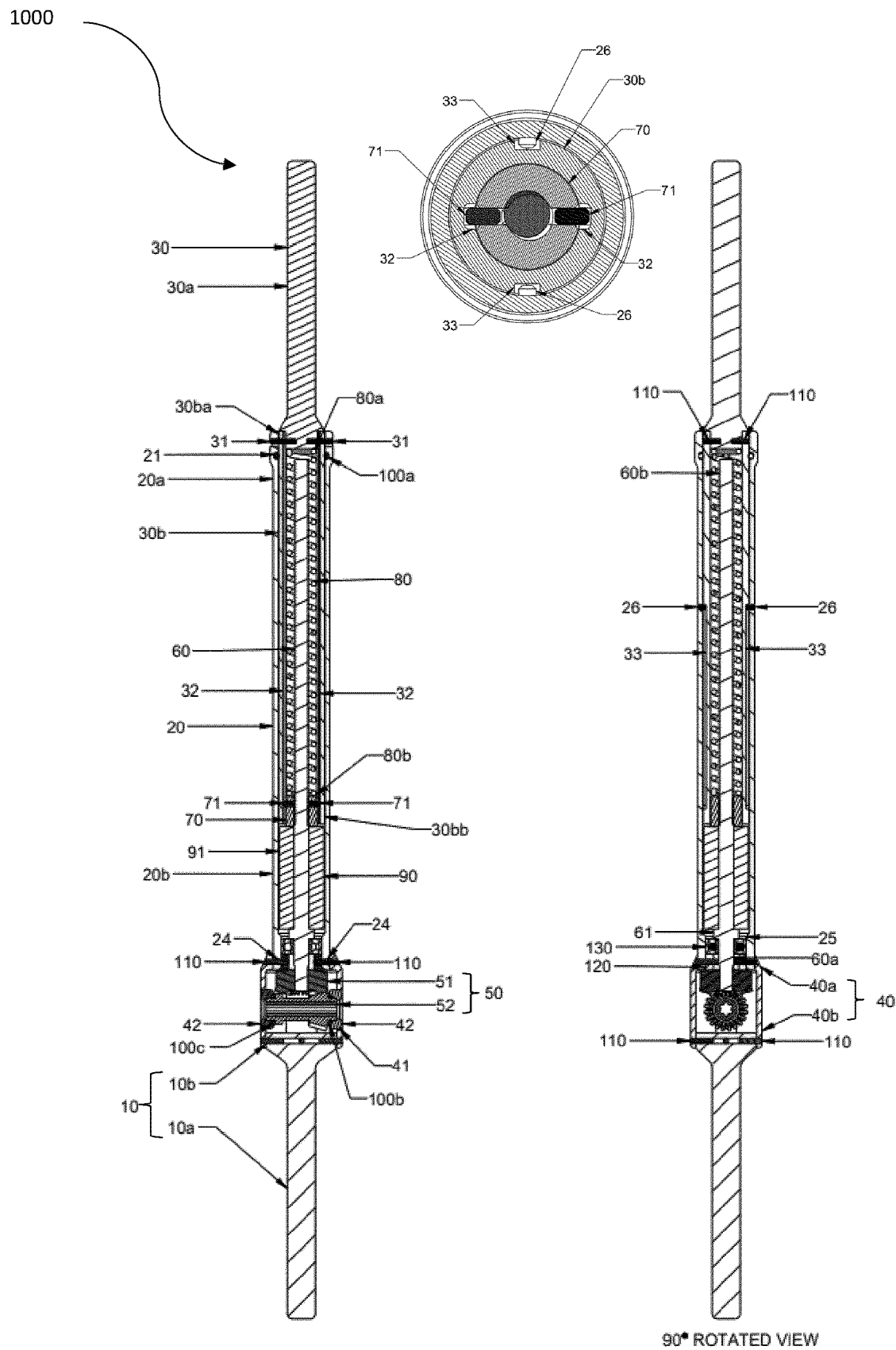
FIG. 16 illustrates a cross sectional view of the eighth embodiment of the constant distraction force driven self-actuating growing rod system (1000) of the present disclosure.

An eighth embodiment of the present system (1000), as illustrated in FIG. 16, is described herein below. The system (1000) of the eighth embodiment comprises at least one static rod component (10); at least one hollow intermediate rod component (20); at least one growth rod component (30); at least one casing (40) housing at least one mechanical biasing mechanism (50); at least one guide rod (60); at least one spring actuator component (70); at least one compression spring component (80) and at least one magnetic field-based spring actuation mechanism (90) as the major components.

Before implanting the system (1000) of the present embodiment in the body of a patient needing correction of a skeletal deformity, a surgeon manually corrects the deformity and immediately affixes the system onto the now-corrected bony anatomy. The pre-compressed compression spring component (80) that is a part of the system (1000) of the present embodiment, applies an active distraction force which continues to support the bony anatomy in the corrected position. However, during the natural growth of the patient, the growth rod component telescopes out of the intermediate rod component (20), which relaxes the pre-compressed compression spring leading to a distraction force deficit in the system (1000). To correct the deficit, a surgeon performs a minimally invasive surgery where they manually cause the compression spring component (80) to regain compression by at least one mechanism selected from the group consisting of magnetic field-based spring actuation mechanism (90) and the mechanical biasing mechanism (50); thereby maintaining an active distraction force onto the system (1000). Therefore, the system (1000) of the present embodiment continues to support the corrected bony anatomy even throughout the natural growth of the patient. Furthermore, the magnetic field-based spring actuation mechanism (90) and the mechanical biasing mechanism (50) used in the system (1000) of the present embodiment are designed in such a way that they are mutually independent and therefore provide the surgeon with a fail-safe tool for correction of skeletal deformity. In one embodiment, the system (1000) of the present embodiment is designed for the correction of deformities in the spine. The detailed construction and working of the system (1000) of the present embodiment is provided herein after.

The static rod component (10) of the present embodiment comprises a first static segment (10a) and a second static segment (10b). The first static segment (10a) is adapted to be affixed at a point below the corrected bony anatomy by at least one fixation element selected from the group consisting of screw(s), hook(s), band(s), wire(s), connector(s), plate(s), staple(s) or any other fixation element typically used in orthopedic surgery. The second static segment (10b) has a substantially cuboidal profile and is affixed to the casing (40) by means of at least one attachment mechanism selected from the group consisting of welding, press-fit, threads, adhesives and connecting pins. In one embodiment, the attachment mechanism of the present embodiment is connecting pins (110). Furthermore, the attachment with the connecting pin(s) (110) is supplemented by welding. It is important to note that the shape of the second static segment (10b) disclosed herein above can be varied on case to case basis.

The hollow intermediate rod component (20) is cylindrical and has a circular cross section and has a body extending between a first end (20a) and a second end (20b). The first end (20a) comprises at least one groove (21) to accommodate at least one dynamic seal plug (100). In one embodiment, the dynamic seal plug (100) is an o-ring. The first end (20a) further comprises at least two radial locking slots (22) with a locking bump (23) each, adapted to confine at least one locking pin (31) affixed to the at least one growth rod component (30) (illustrated in FIG. 18). The second end (20b) comprises at least two holes (24), each adapted to fixedly hold at least one connecting pin (110); thereby fixedly attaching the hollow intermediate rod component to the casing and at least one blocker (120. In one embodiment, the second end (20b) comprises four holes, each adapted to fixedly hold at least one connecting pin (110); thereby fixedly attaching the hollow intermediate rod component to the casing and at least one blocker (120). The second end (20b) further comprises a step down (25) along the internal circumference that is adapted to accommodate at least one bearing (130) and the blocker (120). The body of the hollow intermediate rod component (20) comprises at least two permanently attached guide pins (26) that ride in the slots (33) provided on the growth rod component (30) which ensures that the growth rod component (30) distracts only up to a predetermined distance, as explained later in the document. The hollow intermediate rod component (20) is the outermost sleeve of the system (1000) of the present embodiment and hosts a majority of the components of the system (1000) selected from the group consisting of a part of the growth rod component (30), the guide rod (60), the spring actuator component (70), the compression spring component (80) and the magnetic field-based spring actuation mechanism (90).

The growth rod component (30) comprises a solid, substantially cylindrical first growth segment (30a) and a hollow cylindrical second growth segment (30b). The solid substantially cylindrical first growth segment (30a) is adapted to be affixed at a point above the corrected bony anatomy by at least one fixation element selected from the group consisting of screw(s), hook(s), band(s), wire(s), connector(s), plate(s), staple(s) or any other fixation element typically used in orthopedic surgery. The hollow cylindrical second growth segment (30b) is partially disposed within the intermediate rod component (20) described herein above and is configured to telescope out thereof pursuant to a natural growth of the corrected bony anatomy. Particularly, the hollow cylindrical second growth segment (30b) has a first end (30ba) and second end (30bb). The first end (30ba) comprises at least two holes to facilitate fixed attachment to the first growth segment (30a) by means of at least one attachment mechanism selected from the group consisting of by means of at least one attachment mechanism selected from the group consisting of welding, press-fit, threads, adhesives and connecting pins. In one embodiment, the attachment mechanism of the present embodiment is connecting pins (110). Furthermore, the attachment with the connecting pin(s) (110) is supplemented by welding. In one embodiment, the first end (30ba) comprises four holes to facilitate fixed attachment to the first growth segment. The second end (30bb) abuts the spring actuator component (70) that is threadedly disposed proximal to the mounting end (60a) of the guide rod (60). The second growth segment (30b) has a cylindrical profile and comprises at least two splines (32) extending along the entire internal length. The splines (32) are adapted to ride at least two protrusions (71) on the spring actuator component (70) to prevent rotational motion and ensure linear translation of the spring actuator component (70). Further, the second growth segment (30b) also comprises at least two slots (33) on the external profile, that are designed to enable riding of at least two guide pins (26) fixedly attached on the internal profile of the intermediate rod component (20) to ensure that the hollow cylindrical growth rod component (30b) distracts only up to a predetermined distance. At the junction of the solid, substantially cylindrical first growth segment (30a) and the hollow cylindrical second growth segment (30b), at least two locking pins (31) are present that are adapted to lock the position of the at least one growth rod (30) with respect to the at least one hollow intermediate rod component (20) (illustrated in FIG. 18).

The locking pins (31) at the junction of the solid, substantially cylindrical first growth segment (30a) and the hollow cylindrical second growth segment (30b) and the radial locking slots (22) with a locking bump (23) each present on the hollow intermediate rod component (20) together comprise the locking mechanism of the present embodiment. The locking mechanism is illustrated in detail in FIG. 18. The system of the present embodiment (1000), in its packaged form, is locked. This means that while manufacture and packaging, the growth rod component (30) is inserted inside the intermediate rod component (20) completely and rotated to facilitate locking of the locking pins (31) into the locking slots (22) behind the locking bump (23). Just after a surgeon manually corrects the deformity in a deformed bony anatomy, this locked system is provisionally installed in the body of the patient by provisionally affixing the solid, substantially cylindrical first growth segment (30a) of the growth rod component (30) at a point above the corrected bony anatomy and provisionally affixing the first static segment (20a) of the static rod component (20) at a point below the corrected bony anatomy, to provide a provisionally installed locked constant distraction force driven self-actuating growing rod system (1000). The surgeon then unlocks the provisionally installed locked constant distraction force driven self-actuating growing rod system (1000) by rotating the growth rod component (30) to facilitate the release of the locking pins (31) from the locking slots (22) and the locking bumps (23). Upon release, the growth rod component (30) marginally escapes out of the intermediate rod component (20), as per the space available locally, owing to the inherent force of the at least one compression spring component (80) installed in a pre-compressed state; thereby providing a marginally expanded provisionally installed unlocked constant distraction force driven self-actuating growing rod system (1000). At this stage, even though the pre-compressed spring relaxes by a marginal extent, it still is able to apply an active distraction force on the system (1000). Next, the surgeon permanently installs the marginally expanded provisionally installed unlocked constant distraction force driven self-actuating growing rod system (1000) by permanently affixing the solid, substantially cylindrical first growth segment (30a) of the at least one growth rod component (30) at a point above the corrected bony anatomy and permanently affixing the first static segment (20a) of the at least one static rod component (20) at a point below the corrected bony anatomy to provide a permanently installed unlocked constant distraction force driven self-actuating growing rod system (1000); whereby the presence of at least one compression spring component (80) applies an active distraction force onto the system (1000). The working of the thus installed system (1000), at a point herein after, has been explained earlier in the document and is not repeated again for the sake of brevity. The role of the locking mechanism is therefore to provide a certain degree of control to the user over the involuntary movement of the growing rod component owing to the inherent force of the pre-compressed compression spring component; thereby facilitating effective installation of the system (1000) in the body of the patient.

The substantially cuboidal casing (40) is sandwiched between the static rod component (10) and the hollow intermediate rod component (20) and has a body extending between a first end (40a) and a second end (40b). The first end (40a) of the casing comprises at least two holes to facilitate fixed attachment to the second end (20b) of the intermediate rod component (20) and the blocker (120) by means of at least one attachment mechanism selected from the group consisting of welding, press-fit, threads, adhesives and connecting pins. In one embodiment, the attachment mechanism of the present embodiment is connecting pins (110). Furthermore, the attachment with the connecting pin(s) (110) is supplemented by welding. In one embodiment, the first end (40a) of the casing (40) comprises four holes to facilitate fixed attachment to the second end (20b) of the intermediate rod component (20) and the blocker (120). In one embodiment, the first end (40a) of the casing (40) has a circular entry point. It is important to note that the shape of the first end (40a) of the casing can be varied on case to case basis. The second end (40b) of the casing (40) comprises at least two holes to facilitate fixed attachment to the static rod component (10) by means of at least one attachment mechanism selected from the group consisting of welding, press-fit, threads, adhesives and connecting pins. In one embodiment, the attachment mechanism of the present embodiment is connecting pins (110). Furthermore, the attachment with the connecting pin(s) (110) is supplemented by welding. In one embodiment, the second end (40b) of the casing (40) comprises four holes to facilitate fixed attachment to the static rod component (10). In one embodiment, the cross section of the second end (40b) of the casing (40) is non-circular. It is important to note that the shape of the second end (40b) of the casing (40) can be varied on case to case basis. On the peripheral wall of the body, at least one through-hole (41) is present. It is a characteristic of the casing (40) that it houses at least one mechanical biasing mechanism (50). The mechanical biasing mechanism (50) comprises at least one driven gear (51) and at least one driving gear (52). The driven gear (51) is mounted on the mounting end (60a) of the guide rod (60) and the driving gear (52) is aligned with and operable through the through-hole (41) of the casing (40). The mechanical biasing mechanism (50) is operated by manually rotating the driving gear (52) by means of at least one external driver (53) (not shown in figures) that mates with the driving gear (52). This brings about corresponding rotation in the driven gear (51) which causes the guide rod (60) to rotate, which further causes the spring actuator component (70) to translate linearly, thereby compressing the compression spring component (80) and maintaining an active distraction force onto the system (1000). The driven gear (51) and the driving gear (52) of the present disclosure are selected from a group consisting of bevel gears, worm gears, helical gears, double helical gears, cross-helical gears and spur gears. The casing (40) of the present embodiment comprises at least two annular bushings (42) at the junction between the mechanical biasing mechanism (50) and the through-hole (41) thereof to ensure a fixed mounting of the mechanical biasing mechanism (50) thereon. In one embodiment, the casing (40) of the present embodiment comprises two annular bushings (42), each at the junction between the driving gear (52) and the through-hole (41).

The guide rod (60) of the present embodiment has a mounting end (60*a*) and a free end (60*b*). There is a radially extending step-up projection (61) proximal to the mounting end (60*a*). The mounting end (60*a*) of the guide rod (60) is partially disposed inside the casing (40) and is adapted to mount at least a part of the mechanical biasing mechanism (50). The mounting end (60*a*) of the guide rod (60) has a partially circular and partially non-circular cross section and has a non-threaded profile. In one embodiment, the mounting end (60*a*) of the guide rod (60) mounts the driven gear (51) at the region having the non-circular cross section. The free end (60*b*) of the guide rod (60) has a circular cross section and the profile thereof is partially threaded. The profile of the free end (60*b*) of the guide rod (60) proximal to the radial step-up projection (61), where the magnetic field-based spring actuation mechanism (90) is located, is non-threaded whereas the profile of the rest of the portion is threaded. The guide rod (60) is adapted to rotate when the driven gear (51) rotates. The system of the present embodiment (1000) comprises at least one bearing (130), disposed in the step down portion (25) of the second end (20*b*) of the hollow intermediate rod component (20), coaxial to and abutting the radially extending step-up projection (61) at the mounting end (60*a*) of the guide rod (60). The bearing (130) is adapted to facilitate free rotation of the guide rod (60). The bearing (130) of the present embodiment is at least one selected from the group consisting of annular roller bearing and axial thrust bearing. The system of the present embodiment (1000) further includes at least one blocker (120) having an annular profile and comprising at least two holes to facilitate fixed attachment of the blocker (120) with the second end (20*b*) of the hollow intermediate rod component (20) and the first end (40*a*) of the casing (40), by means of at least one attachment mechanism selected from the group consisting of welding, press-fit, threads, adhesives and connecting pins. In one embodiment, the attachment mechanism of the present embodiment is connecting pins (110). Furthermore, the attachment with the connecting pin(s) (110) is supplemented by welding. In one embodiment, the blocker (120) comprises four holes to facilitate fixed attachment of the blocker (120) with the second end (20*b*) of the hollow intermediate rod component (20) and the first end (40*a*) of the casing (40). The blocker (120) of the present embodiment is adapted to provide a resting surface to the bearing (130).

The spring actuator component (70) of the present embodiment abuts the second end (30*bb*) of the hollow cylindrical second growth segment (30*b*) of the growth rod component (30) and is sandwiched between the compression spring component (80) and the magnetic spring actuator component (90). The spring actuator component (70) has an internally threaded bore, which enables the spring actuator component (70) to ride over the threaded portion of the guide rod (60), consequent to the rotation thereof. However, due to the presence of the at least two protrusions (71) thereon, that ride on the spline (32) of the hollow second growth segment (30*b*) of the growth rod component (30), rotational movement of the spring actuator component (70) is prevented, ensuring that the spring actuator component (70) only translates linearly.

The compression spring component (80) of the present embodiment comprises at least one compression spring that is coaxially disposed within the hollow second growth segment (30*b*) of the growth rod component (30), around the guide rod (60). The compression spring component (80) abuts the first growth segment (30*a*) of the growth rod component (30) at a first end (80*a*) and rests on the at least one spring actuator component (70) at a second end (80*b*). The compression spring (80) is installed in the system of the present disclosure (1000) in a pre-compressed state and is adapted to apply an active distraction force onto the system (1000). The compression spring component (80) of the present disclosure is at least one selected from the group consisting of a helical coil spring, a conical coil spring, a leaf spring, a constant force spring, a disc spring, a constant rate spring, an extension coil spring and a constant torque spring.

The magnetic field-based spring actuation mechanism (90) of the present disclosure comprises at least one magnetic spring actuator component (91) and at least one magnetic field generating component (not shown in the figures). The magnetic spring actuator component (91) is disposed within the hollow portion of the intermediate rod component (20) and sandwiched between the spring actuator component (70) on one end and the radially extending step-up projection (61) of the guide rod (60). The magnetic spring actuator component (91) is adapted to move in a rotational motion under the stimulus of the magnetic field generating component which is located outside of the body and. The rotational motion of the magnetic spring actuator component (91) causes the guide rod (60) to rotate which in turn causes the spring actuator component (70) to translate linearly. This motion of the spring actuator component (70) compresses the compression spring component (80); thereby maintaining an active distraction force onto the system (1000).

The system of the present embodiment comprises a plurality of dynamic seal plugs (100) with corresponding grooves (21) for receiving them. In one embodiment (1000), the system of the present embodiment comprises three dynamic seal plugs. The first seal plug (100*a*) is disposed between the inner circumference of the intermediate rod component (20) and the outer circumference of the first end (30*ba*) of the hollow second growth segment (30*b*) of the growth rod component (30) and is adapted to prevent movement of at least one contaminant in and out of the system (1000). The second (100*b*) and the third seal plugs (100*c*) are disposed in the casing (40) below the bushings (42) and are adapted to prevent the inflow of bodily fluids into the system (1000). In one embodiment, the dynamic seal plug (100) of the present embodiment is an o-ring.

Figure 17:
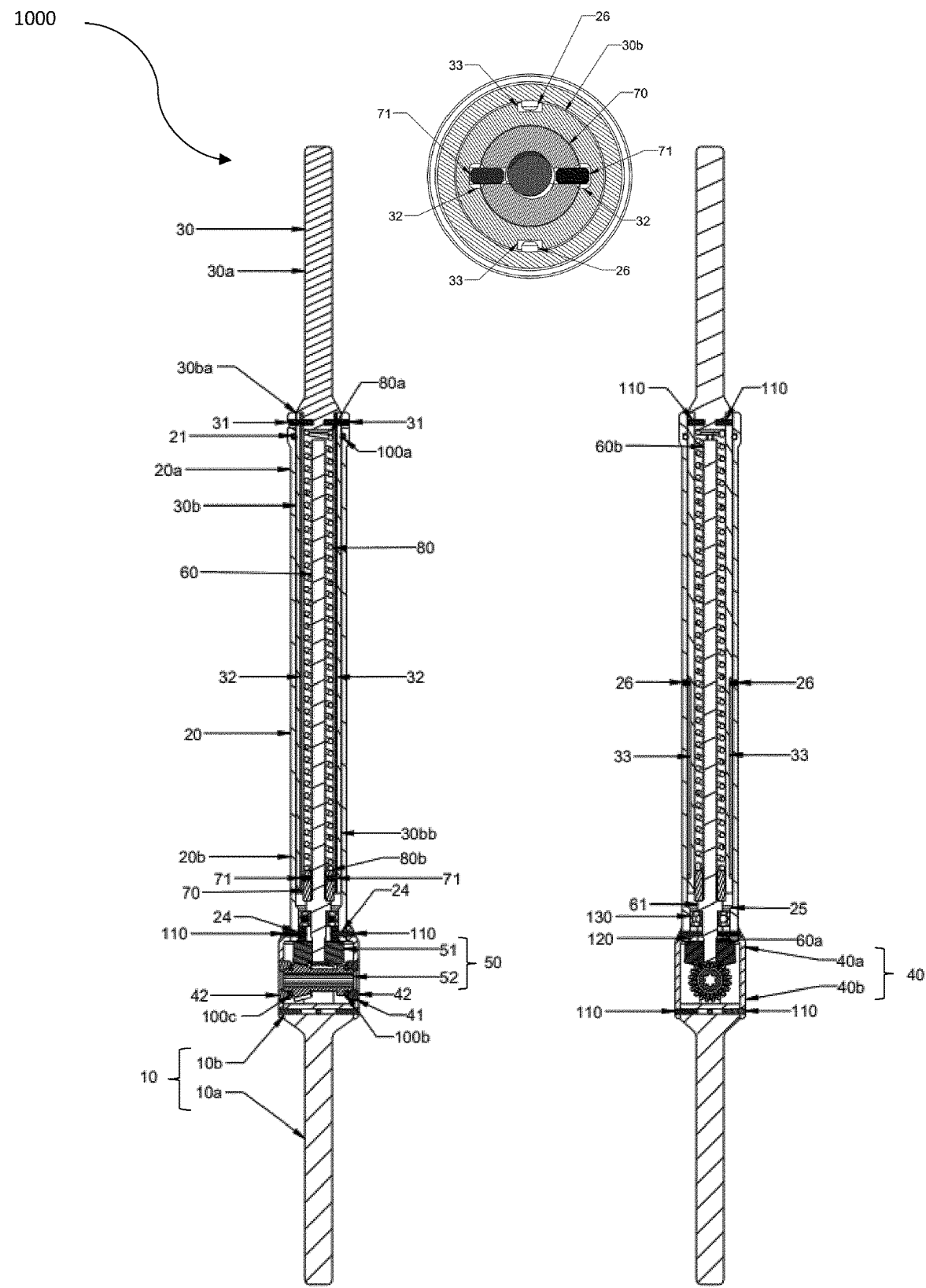
FIG. 17 illustrates a cross sectional view of the ninth embodiment of the constant distraction force driven self-actuating growing rod system (1000) of the present disclosure.
Figure 18:
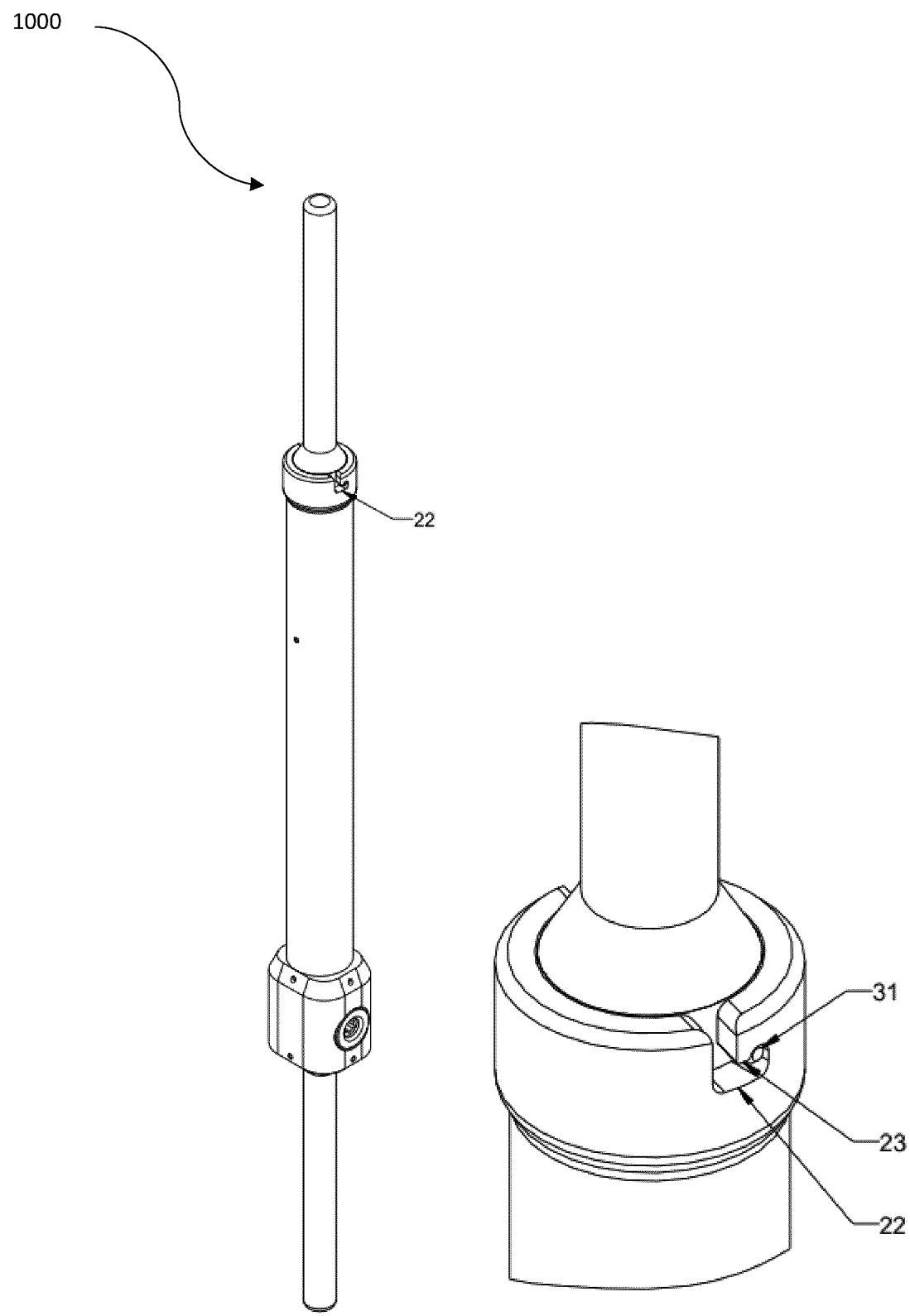
FIG. 18 illustrates a perspective view of the locking system of the embodiment eight and nine of the constant distraction force driven self-actuating growing rod system (1000) of the present disclosure.

A ninth embodiment of the present system (1000), as illustrated in FIG. 17, is described herein below. The system of the ninth embodiment comprises all the components discussed in the eighth embodiment, except for the magnetic field-based spring actuation mechanism. The system of the ninth embodiment comprises at least one static rod component (10); at least one hollow intermediate rod component (20); at least one casing (40) housing a mechanical biasing mechanism (50); at least one growth rod component (30); at least one guide rod (60); at least one bearing (130); at least one blocker (120); at least two annular bushings (42); at least one spring actuator component (70); at least one compression spring component (80) and a plurality of dynamic seal plugs (100) as the major components.

The working of the system (1000) of the present embodiment and its components is similar to that of the eighth embodiment, except that the distraction force deficit created during the natural growth of the patient is corrected by causing the re-compression of the compression spring component (80) by means of the mechanical biasing mechanism (50) only (without any contribution from the magnetic field-based spring actuation mechanism).

The profiling and construction of most of the components in the system of embodiment nine, is the same as that of embodiment eight. However, owing to the absence of the magnetic field-based spring actuation mechanism, the profiling and construction of certain components in the system of embodiment nine, such as the profile of the guide rod (60) and the juxtaposition of the spring actuator component (70) varies as described herein below. The guide rod (60) of the system of embodiment nine has a mounting end (60a) and a free end (60b) and a radially extending step-up projection (61) therebetween, proximal to the mounting end (60a) as discussed in embodiment eight. However, the free end (60b) of the guide rod (60) of embodiment nine, having a circular cross section, has an entirely threaded profile. The spring actuator component (70) of the present embodiment abuts the second end (30bb) of the hollow cylindrical second growth segment (30b) of the growth rod component (30) as in embodiment eight. However, in embodiment nine, the spring actuator component (70) is sandwiched between the compression spring component (80) at one end and the radially extending step-up projection (61) of the guide rod (60) at the other end.

Figure 19:
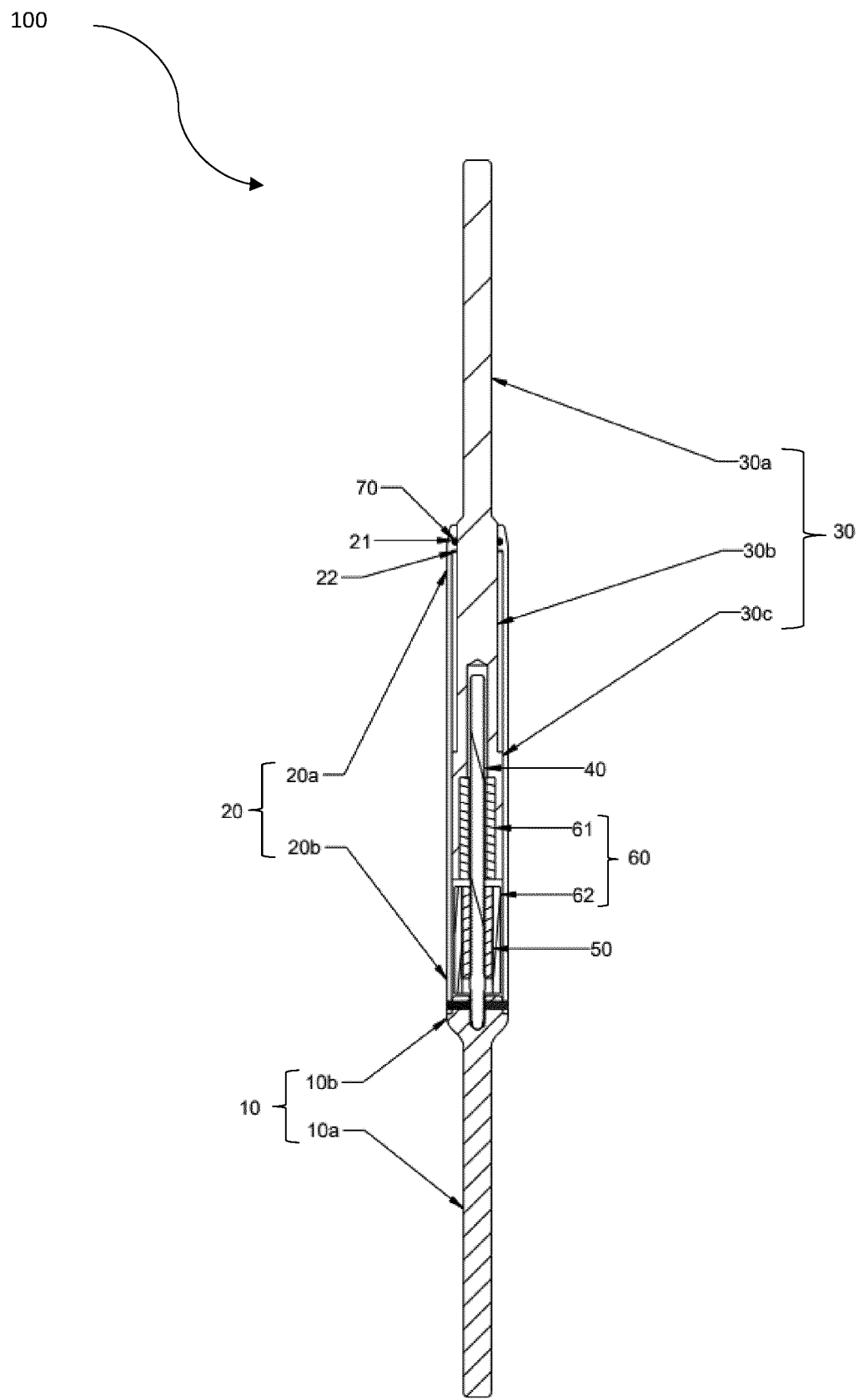
FIG. 19 illustrates a cross sectional view of the tenth embodiment of the constant distraction force driven self-actuating growing rod system (100) of the present disclosure.

A tenth embodiment of the present system (100), as illustrated in FIG. 19, is described herein below. The system (100) of the tenth embodiment comprises at least one static rod component (10); at least one hollow intermediate rod component (20); at least one growth rod component (30); at least one guide rod (40), at least one spring actuator component (50) and a magnetic mechanism (60) as the major components.

The static rod component (10) comprises at least one first static segment (10a) and at least one second growth segment (10b). The first static segment (10a) is adapted to be affixed at a point below the corrected bony anatomy by at least one fixation element selected from the group consisting of screw(s), hook(s), band(s), wire(s), connector(s), plate(s), staple(s) or any other fixation element typically used in orthopedic surgery. The second static segment (10b) is adapted to be disposed within and fixedly attached to the intermediate rod component (20) by means of at least one attachment mechanism selected from the group consisting of welding, press-fit, threads, adhesives and connecting pins. In one embodiment, the attachment mechanism of the present embodiment is connecting pins (110). Furthermore, the attachment with the connecting pin(s) (110) is supplemented by welding.

The intermediate rod component (20) is hollow and cylindrical and comprises a first end (20a) and a second end (20b). The first end (20a) comprises at least one groove (21) to accommodate at least one dynamic seal plug (70) and a physical stop (22). In one embodiment, the dynamic seal plug (70) is an o-ring. The second end (20b) is adapted to allow the growth rod component (30) to telescope within.

The guide rod (40) is threadedly attached to the static rod component (10) and the attachment is supplemented by welding. The guide rod (40) has a solid cylindrical profile and is threaded across the entirety of the outer circumference.

The growth rod component (30) is cylindrical and comprises three segments. The first segment (30a) is adapted to be affixed at a point above the corrected bony anatomy by at least one fixation element selected from the group consisting of screw(s), hook(s), band(s), wire(s), connector(s), plate(s), staple(s) or any other fixation element typically used in orthopedic surgery. The second segment (30b) is capable of telescoping within the intermediate rod component (20) while providing a sealing surface to the dynamic seal plug (70) installed in the intermediate rod component (20). The third segment (30c) has a stepped up outer diameter which is also adapted to telescope inside the intermediate rod component (20) while providing a physical stop (22) upon maximum distraction. There are two types of bore on the growth rod component (30). The first bore houses a first magnet (61). The second bore provides a passage for disposition of the guide rod (40) emerging from the static rod component (10). In one embodiment, the first magnet (61) is rigidly connected to the growth rod component (30) which prevents relative axial or rotational motion therebetween. In a second embodiment, the first magnet (61) is partially constrained and allows relative rotational motion and prevents axial motion.

The spring actuator component (50) comprises at least one threaded internal bore which enables the spring actuator component (50) to be installed on the guide rod (40) such that the spring actuator component (50) rides over the threads of the guide rod (40). Concentric to the spring actuator component (50), a second magnet (62) is installed. The magnets (61 and 62) are positioned in a way which ensures that they repel each other more and more as axial distance between them reduces. The first magnet (61) and the second magnet (62) together form the magnetic mechanism (60) of the present embodiment. Therefore during the natural growth of the patient, the growth rod component (30) telescopes out of the intermediate rod component (20), which increases the distance between magnet one (61) and magnet two (62), which consequently decreases the repulsion force there between. An external magnetic field generating component (not shown in the figures) is used to move the second magnet (62) towards the first (61) and consequently decrease the distance between the two magnets. As a result, the repulsion force between the two magnets increases which provides a distraction force to the growth rod component (30); thereby maintaining an active distraction force onto the system (100). Therefore, the system (100) of the present embodiment continues to support the corrected bony anatomy even throughout the natural growth of the patient. In one embodiment, the system (100) of the present embodiment is designed for the correction of deformities in the spine.

It is important to note that the locking mechanism described in the eighth embodiment can also be incorporated in the rest of the embodiments of the present disclosure.

While embodiments of the present invention have been illustrated and described, various modifications can be made without departing from the scope of the invention. Therefore, the invention should not be limited, except for the following claims and equivalents thereof.

The afore-stated components of the system of the present disclosure are manufactured from biocompatible materials. Further, the components of the system (100) of the present disclosure are manufactured from at least one material selected from the group that includes but is not limited to metal(s), metal alloys, polymers and non-Newtonian fluids. For the purpose of the present disclosure, the term metal is at least one selected from the group that includes but is not limited to titanium, cobalt-chromium-molybdenum, and stainless steel or any other metal or metal alloy suitable from biocompatibility and strength perspective. For the purpose of the present disclosure, the term polymers is at least one selected from the group that includes but is not limited to high density polyethylene (HDPE), polyurethane, polycarbonate urethane, ultra-high molecular weight polyethylene (UHMWPE), polyethylene terephthalate (PET), polyether ether ketone (PEEK) and silicone or any other polymer suitable from biocompatibility and strength perspective. All the components of the various systems of the present disclosure may be fabricated separately and attached together using conventional manufacturing techniques.

Technical Advantages and Economic Significance

The technical advantages and economic significance of the constant distraction force driven self-actuating growing rod systems, of the present disclosure are presented herein after:

- The present system does not hamper the natural growth of the patient;
- The present system provides multiple point anchoring to the bony anatomy to reduce the chances of rod breakage;
- The present system constantly adapts according to the natural growth of the patient, providing distractions and distraction forces exactly required by the patient's body;
- In the present system, an external instrument generates magnetic field and interacts with the magnetic component without any physical connection by the phenomenon of magnetic coupling/attraction; thereby minimizing surgical intervention;
- The present system (100) causes an improvement in the quality of life of the patient due to non-repetitive surgical distraction;
- The present system does not contain any fluids; thereby eliminating the chance of fluid leakage;
- The present system light-weight and economical; and
- The present system provides two options or mechanisms for reinstating the distraction force, which can be used interchangeably; thereby making the present system fail-safe.

We claim:

1. A constant distraction force driven self-actuating growing rod system (1000) for implantation on a corrected bony anatomy, the system (1000) comprising:
   a. at least one static rod component (10);
   b. at least one hollow intermediate rod component (20);
   c. at least one growth rod component (30) being partially disposed within the at least one intermediate rod component (20);
   d. at least one casing (40) being sandwiched between the at least one static rod component (10) and the at least one hollow intermediate rod component (20) and characterised by housing at least one mechanical biasing mechanism (50);
   e. at least one guide rod (60) being partially disposed within the at least one casing (40) whereby at least a part of the at least one mechanical biasing mechanism (50) is mounted thereon;
   f. at least one spring actuator component (70) being disposed over the at least one guide rod (60) and adapted to ride thereover by linear translation;
   g. at least one compression spring component (80) housed inside the at least one intermediate rod component (20) abutting the at least one spring actuator component (70) and adapted to apply an active distraction force onto the system (1000); and
   h. at least one magnetic field-based spring actuation mechanism (90);

whereby during the natural growth of the corrected bony anatomy, a part of the at least one growth rod component (30) telescopes out of the at least one intermediate rod component (20), creating a distraction force deficit in the system (1000), said distraction force deficit being corrected by causing the at least one compression spring component (80) to get compressed; thereby maintaining an active distraction force onto the system (1000).

2. The constant distraction force driven self-actuating growing rod system (1000) as claimed in claim 1, wherein the at least one static rod component (10) comprises a first static segment (10*a*) and a second static segment (10*b*), wherein the first static segment (10*a*) is adapted to be affixed at a point below the corrected bony anatomy and the second static segment (10*b*) has a substantially cuboidal profile and is fixedly attached to the at least one casing (40).

3. The constant distraction force driven self-actuating growing rod system (1000) as claimed in claim 1, wherein the at least one hollow intermediate rod component (20) is cylindrical, has a circular cross section and has a body extending between a first end (20*a*) and a second end (20*b*), wherein the first end (20*a*) comprises at least one groove (21) to accommodate at least one dynamic seal plug (100) and at least two radial locking slots (22) with a locking bump (23) each, adapted to confine at least one locking pin (31) affixed to the at least one growth rod component (30) and the second end (20*b*) comprises at least two holes (24) adapted to fixedly hold at least one connecting pin (110) each for fixed attachment to the at least one casing (40) and at least one blocker (120) and said second end (20*b*) further comprising a step down (25) along the internal circumference adapted to accommodate at least one bearing (130) and the at least one blocker (120) and wherein the body of the at least one hollow intermediate rod component (20) comprises at least two guide pins (26) fixedly attached on the internal profile thereof.

4. The constant distraction force driven self-actuating growing rod system (1000) as claimed in claim 1, wherein the at least one growth rod component (30) comprises a solid, substantially cylindrical first growth segment (30*a*) and a hollow cylindrical second growth segment (30*b*), whereby at least two locking pins (31) are present at the junction thereof and are adapted to lock the position of the at least one growth rod (30) with respect to the at least one hollow intermediate rod component (20), whereby the solid substantially cylindrical first growth segment (30*a*) is adapted to be affixed at a point above the corrected bony anatomy and the hollow cylindrical second growth segment (30*b*) is partially disposed within the at least one intermediate rod component (20) and extends from a first end (30*ba*) to a second end (30*bb*), wherein the first end (30*ba*) is fixedly attached to the solid substantially cylindrical first growth segment (30*a*) and the second end (30*bb*) abuts the at least one spring actuator component (70) threadedly disposed on the at least one guide rod (60), said at least one hollow cylindrical second growth segment (30*b*) further comprising:

a. at least two splines (32) extending along the entire internal length thereof and adapted to ride at least two protrusions (71) and prevent rotational motion and ensure linear translation of the at least one spring actuator component (70); and
b. at least two slots (33) on the external profile adapted to enable the riding of at least two guide pins (26) fixedly attached on the internal profile of the at least one intermediate rod component (20) to ensure that the hollow cylindrical second growth segment (30*b*) of the at least one growth rod component (30) distracts only up to a predetermined distance.

5. The constant distraction force driven self-actuating growing rod system (1000) as claimed in claim 1, wherein the at least one guide rod (60) extends between a mounting end (60*a*) and a free end (60*b*), is rotatable, and comprises a radially extending step-up projection (61) proximal to the mounting end (60*a*), wherein the mounting end (60*a*) of the guide rod (60) has a partially circular and partially non-circular cross section and a non-threaded profile and the free end (60*b*) of the at least one guide rod (60) has a circular cross section and a non-threaded profile at the region proximal to the radial step-up projection (61), comprising a part of the at least one magnetic field-based spring actuation mechanism (90) and the rest of the profile being threaded.

6. The constant distraction force driven self-actuating growing rod system (1000) as claimed in claim 1, further comprising:
a. at least one bearing (130) selected from the group consisting of annular roller bearing and axial thrust bearing, being disposed in the step down portion (25) of the second end (20*b*) of the at least one hollow intermediate rod component (20), coaxial to and abutting the radially extending step-up projection (61) at the mounting end (60*a*) of the at least one guide rod (60) and adapted to facilitate free rotation of the at least one guide rod (60); and
b. at least one blocker (120) having an annular profile and comprising at least two holes to facilitate fixed attachment to the at least one hollow intermediate rod component (20) and the at least one casing (40) and adapted to provide a resting surface to the at least one bearing (130).

7. The constant distraction force driven self-actuating growing rod system (1000) as claimed in claim 1, wherein the at least one spring actuator component (70) abuts the second end (30*bb*) of the at least one hollow cylindrical second growth segment (30*b*) of the at least one growth rod component (30) and is sandwiched between the at least one compression spring component (80) and the at least one magnetic spring actuator component (90); said at least one spring actuator component (70) is disposed over the at least one guide rod (60) via an internally threaded bore therein and is adapted to ride over the at least one guide rod (60), consequent to the rotation thereof; said at least one spring actuator component (70) further comprising at least two protrusions (71) that abut the spline (32) of the hollow second growth segment (30*b*) of the at least one growth rod component (30) to prevent rotational motion and ensuring linear translation of the at least one spring actuator component (70).

8. The constant distraction force driven self-actuating growing rod system (1000) as claimed in claim 1, wherein the at least one compression spring component (80) comprises at least one compression spring being concentrically disposed within the hollow second growth segment (30*b*) of the at least one growth rod component (30), around the at least one guide rod (60) and abutting the first growth segment (30*a*) of the at least one growth rod component (30) at a first end (80*a*) and resting on the at least one spring actuator component (70) at a second end (80*b*), wherein said at least one compression spring (80) is installed in a pre-compressed state and during the natural growth of the corrected bony anatomy, the telescoping movement of the at least one growth rod component (30) causes the pre-compressed compression spring component (80) to relax; thereby creating a distraction force deficit in the system (1000); and wherein said at least one compression spring component (80) is at least one selected from the group consisting of a helical coil spring, a conical coil spring, a leaf spring, a constant force spring, a disc spring, a constant rate spring, an extension coil spring and a constant torque spring.

9. The constant distraction force driven self-actuating growing rod system (1000) as claimed in claim 1, wherein the at least one mechanical biasing mechanism (50) comprises at least one driven gear (51) mounted on the mounting end (60*a*) of the at least one guide rod (60); and at least one driving gear (52) aligned with and operable through the at least one through-hole (41) of the at least one casing (40) accompanied by at least one bushing (42) at the junction thereof, whereby manually operating the at least one mechanical biasing mechanism (40) by manually rotating the at least one driving gear (52) by means of at least one external driver (53) that mates with the at least one driving gear (52), causes corresponding rotation in the at least one driven gear (51), rotating the at least one guide rod (60) and causing linear translation of the at least one spring actuator component (70), thereby compressing the at least one compression spring component (80) and maintaining an active distraction force onto the system (1000), wherein said at least one driven gear (51) and the at least one driving gear (52) are selected from a group consisting of bevel gears, worm gears, helical gears, double helical gears, cross-helical gears and spur gears.

10. The constant distraction force driven self-actuating growing rod system (1000) as claimed in claim 1, at least one magnetic field-based spring actuation mechanism (90) comprises at least one magnetic spring actuator component (91) and at least one magnetic field generating component, wherein the at least one magnetic spring actuator component (91) is disposed within the hollow portion of the at least one intermediate rod component (20) and is adapted to move in a rotational motion under the stimulus of the at least one magnetic field generating component (92) and consequently rotate the at least one guide rod (60), causing linear translation of the at least one spring actuator component (70); thereby compressing the at least one compression spring component (80) and maintaining an active distraction force onto the system (1000) and wherein the magnetic field generating component (92) is outside the body.

11. The constant distraction force driven self-actuating growing rod system (1000) as claimed in claim 1, further comprising a plurality of dynamic seal plugs (100), wherein a first seal plug (100*a*) is disposed between an inner circumference of the at least one intermediate rod component (20) and the outer circumference of the first end (30*ba*) of the hollow second growth segment (30*b*) of the at least one growth rod component (30) and is adapted to prevent movement of at least one contaminant in and out of the system (1000), a second (100*b*) and the third seal plug (100*c*) are disposed in the at least one casing (40) below the at least one bushing (42) and are adapted to prevent the inflow of bodily fluids into the system (1000).

12. The constant distraction force driven self-actuating growing rod system (1000) as claimed in claim 1, wherein said magnetic field-based spring actuation mechanism (90) is absent and wherein the at least one guide rod (60) extends between a mounting end (60*a*) and a free end (60*b*), is rotatable, and comprises a radially extending step-up projection (61) proximal to the mounting end (60*a*), wherein the free end (60*b*) of the at least one guide rod (60) has a cylindrical profile and is threaded along the entire outer circumference and the mounting end (60*a*) of the at least one guide rod (60) has a non-threaded profile and a partially circular and partially non-circular cross section and wherein the at least one spring actuator component (70) abuts the second end (30*bb*) of the hollow cylindrical second growth segment (30*b*) of the at least one growth rod component (30) and is sandwiched between the at least one compression spring component (80) at one end and the radially extending step-up projection (61) of the at least one guide rod (60) at the other end; said at least one spring actuator component (70) is disposed over the at least one guide rod (60) via an internally threaded bore therein and is adapted to ride over the at least one guide rod (60), consequent to the rotation thereof; said at least one spring actuator component (70) further comprising at least two protrusions (71) that abut the spline (32) of the hollow second growth segment (30*b*) of the at least one growth rod component (30) to prevent rotational motion and ensuring linear translation of the at least one spring actuator component (70).

13. A method of operating at least one constant distraction force driven self-actuating growing rod system (1000), comprising:
a. provisionally installing the at least one locked constant distraction force driven self-actuating growing rod system (1000) by provisionally affixing a solid, substantially cylindrical first growth segment (30*a*) of at least one growth rod component (30) at a point above a manually corrected bony anatomy and provisionally affixing a first static segment (20*a*) of at least one static rod component (20) at a point below the corrected bony anatomy to provide a provisionally installed locked constant distraction force driven self-actuating growing rod system (1000);
b. unlocking the provisionally installed locked constant distraction force driven self-actuating growing rod system (1000) by rotating the at least one growth rod component (30) to facilitate the release of at least two locking pins (31), present at the junction of the solid, substantially cylindrical first growth segment (30*a*) and a hollow cylindrical second growth segment (30*b*) of the growth rod component (30), from at least two radial locking slots (22) and at least one locking bump (23) each and to further allow the at least one growth rod component (30) to marginally escape out of the at least one intermediate rod component (20) and provide a marginally expanded, provisionally installed unlocked constant distraction force driven self-actuating growing rod system (1000);
c. permanently installing the marginally expanded provisionally installed unlocked constant distraction force driven self-actuating growing rod system (1000) by permanently affixing the solid, substantially cylindrical first growth segment (30*a*) of the at least one growth rod component (30) at a point above the corrected bony anatomy and permanently affixing the first static segment (20*a*) of the at least one static rod component (20) at a point below the corrected bony anatomy to provide a permanently installed unlocked constant distraction force driven self-actuating growing rod system (1000); whereby the presence of at least one compression spring component (80) applies an active distraction force onto the system (1000);
d. telescoping of at least a part of the at least one growth rod component (30) out of the at least one intermediate rod component (20) during the natural growth of the corrected bony anatomy, causing the at least one compression spring component (80) to relax; thereby creating a distraction force deficit in the system (1000); said distraction force deficit being corrected by compressing the at least one compression spring component (80) by means of at least one mechanism selected from the group consisting of at least one magnetic field-based spring actuation mechanism (90) comprising at least one magnetic spring actuator component (91) and at least one magnetic field generating component (92) and at least one mechanical biasing mechanism (50) comprising at least one driven gear (51) and at least one driving gear (52); thereby maintaining an active distraction force onto the system (1000).

14. The method of operating the constant distraction force driven self-actuating growing rod system (1000) of claim 13, wherein the step of correction of the distraction force deficit by compressing the at least one compression spring component (80) is done only by the at least one mechanical biasing mechanism (50) comprising at least one driven gear (51) and at least one driving gear (52); thereby maintaining an active distraction force onto the system (1000).

15. The method of operating the constant distraction force driven self-actuating growing rod system (1000) of claim 13, wherein manually rotating the at least one driving gear (51) by means of at least one external driver (53) that mates with the at least one driving gear (52), causes corresponding rotation in the at least one driven gear (51), causing rotation of at least one guide rod (60) and linear translation of at least one spring actuator component (70), thereby compressing the at least one compression spring component (80) and maintaining an active distraction force onto the system (1000).

16. The method of operating the constant distraction force driven self-actuating growing rod system (1000) of claim 13, wherein the at least one magnetic spring actuator component (91) is adapted to move in a rotational motion under the stimulus of at least one magnetic field generating component (92) and consequently rotate the at least one guide rod (60), causing linear translation of the at least one spring actuator component (70); thereby compressing the at least one compression spring component (80) and maintaining an active distraction force onto the system (1000).

17. The method of operating the constant distraction force driven self-actuating growing rod system (1000) of claim 13, wherein rotational motion of the at least one spring actuator component (70), consequent to rotation of the at least one guide rod (60), is prevented and linear translation of the at least one spring actuator component (70) is effected by causing at least two protrusions (71) affixed onto the at least one spring actuator component (70) to ride on splines (32) partially extending along the internal length of the hollow second growth segment (30*b*) of the at least one growth rod component (30).

18. The method of operating the constant distraction force driven self-actuating growing rod system (1000) of claim 13, wherein distraction of the at least one growth rod component (30) is restricted to a pre-determined distance by causing at least two guide pins (26) affixed on the internal profile of the at least one intermediate rod component (20)

to ride on at least two slots (33) on the external profile of the second growth segment (30*b*) of said at least one growth rod component (30).

\* \* \* \* \*